US008048659B1

(12) United States Patent
Leif et al.

(10) Patent No.: US 8,048,659 B1
(45) Date of Patent: Nov. 1, 2011

(54) CONJUGATED POLYMER TAG COMPLEXES

(76) Inventors: Robert C. Leif, San Diego, CA (US); Lidia Vallarino, Richmond, VA (US)

( * ) Notice: Subject to any disclaimer, the term of this patent is extended or adjusted under 35 U.S.C. 154(b) by 1207 days.

(21) Appl. No.: 10/110,114

(22) PCT Filed: Oct. 7, 2000

(86) PCT No.: PCT/US00/27787
§ 371 (c)(1),
(2), (4) Date: Aug. 23, 2002

(87) PCT Pub. No.: WO01/27625
PCT Pub. Date: Apr. 19, 2001

Related U.S. Application Data

(60) Provisional application No. 60/158,718, filed on Oct. 8, 1999.

(51) Int. Cl.
*G01N 33/53* (2006.01)
(52) U.S. Cl. ........ 435/174; 435/7.1; 435/7.21; 436/518; 422/50; 424/9.322; 424/78.08
(58) Field of Classification Search ................ 435/174; 436/518; 422/55; 424/9.322, 78.08
See application file for complete search history.

(56) References Cited

U.S. PATENT DOCUMENTS

| | | | |
|---|---|---|---|
| 4,876,190 A | 10/1989 | Recktenwald | |
| 5,373,093 A | 12/1994 | Vallarino et al. | |
| 5,696,240 A * | 12/1997 | Vallarino et al. | 534/15 |
| 5,736,410 A | 4/1998 | Zarling et al. | |
| 5,891,741 A | 4/1999 | Siiman et al. | |
| 5,976,790 A | 11/1999 | Pinkel et al. | |

FOREIGN PATENT DOCUMENTS

| | | | |
|---|---|---|---|
| WO | WO 92/08790 | * | 5/1992 |
| WO | WO 95/02184 | * | 1/1995 |

OTHER PUBLICATIONS

Yamada et al. (Carbohydrate Research, 305, 1998, pp. 443-461).*
Hiort et al. (Biochemistry, 1996, 35, pp. 12354-12362).*
Heidmann and Koster (Makromol. Chem., 181, 1980, pp. 2495-2506, Abstract Only).*
A. Schwartz and E. Fernandez-Repollet, "Development of clinical standards for flow cytometry", Annals N.Y. Academy of Science 677 pp. 28-39, 1993.
H.M. Shapiro, Practical Flow Cytometry, Third Edition p. 91, Wiley-Liss, New York, N.Y 1995.
J. R. Lakowicz, "Principles of Fluorescence Spectroscopy" p. 373-374 , Plenum Press, 1983. New York.
J. Haralambidis et al., "The Synthesis of Polyamide-Oligonucleotide Conjugate Molecules", Nucleic Acids Research 18, pp. 493-499, 1990 A.
J. Haralambidis et al., "The Preparation of Polyamide-Oligonucleotide Probes Containing Multiple Non-radioactive Labels", Nucleic Acids Research 18, pp. 501-505, 1990 B.

R. P. Haugland, Handbook of Fluorescent Probes and Research Chemicals CD, 14.5 Products, 7th edition, Molecular Probes, Inc., Eugene, Oreg. 97402, 1999.
J. J. Peterson and C. F. Meares, "Cathepsin Substrates as Cleavable Peptide Linkers in Bioconjugates, . . . ", Bioconjugate Chemistry 9, pp. 618-626, 1998.
J. J Peterson. and C. F. Meares, "Enzymatic Cleavage of Peptide-Linked Radiolabels from Immunoconjugates", Bioconjugate Chemistry 10, pp. 553-557, 1999.
H. Takalo et al. Synthesis of europium(III) chelates suitable for labeling of bioactive molecules, Bioconjugate Chemistry 5, pp. 278-282, 1994.
JB Lamture and TG Wensel, "Intensely luminescent immunoreactive conjugates of proteins and dipicolinate-based polymeric Tb (III) chelates", Bioconjug Chem. 6, pp. 88-92, 1995.
M Kwiatkowski et al, "Solid-phase synthesis of chelate-labeled oligonucleotides: application in triple-color ligase-mediated gene analysis", Nucleic Acids Research 22, pp. 2604-2611, 1994.
H Salo et al. "Disulfide-Tethered Solid Supports for Synthesis of Photoluminescent Oligonucleotide Conjugates: Hydrolytic Stability and Labeling on the Support", Bioconjugate Chemistry 9, pp. 365-371, 1998.
RC Leif et al. "Production, Fixation, and Staining of Cells on Slides for Maximum Photometric Sensitivity". Proceedings of Biochemical Diagnostic Instrumentation, Progress in Biomedical Optics. R. F. Bonner, G. E. Cohn, T. M. Laue, and A. V. Priezzhev Eds.; SPIE Proceedings Series 2136, pp. 255-262, 1994.
N Sabbatini et al. "Radiative and Nonradiative Transitions in the Eu(III) Hexaaza Macrocyclic Complex [Eu(C22H26N6)(CH3COO)](CH3COO)Cl2H2O," J. Phys. Chem., vol. 91, pp. 4681-4685, 1987.
AJ Bromm Jr et al. "The Addition of a Second Lanthanide Ion to Increase the Luminescence of Europium(III) Macrocyclic Complexes", Proceedings of Optical Diagnostics of Living Cells II, D. L. Farkas, R. C. Leif, B. J. Tromberg, Editors, SPIE Progress in Biomedical Optics,. A. Katzir series Editor, vol. 3604, ISBN 0-8194-3074-9, pp. 263-272, 1999.
JR Quagliano et al., "Methods to Increase the Luminescence of Lanthanide(III) Macrocyclic Complexes", Optical Diagnostics of Living Cells III, D. L. Farkas and R. C. Leif, Editors, Proceedings of SPIE vol. 3921. pp. 124-133, 2000.

(Continued)

*Primary Examiner* — Lisa Cook
(74) *Attorney, Agent, or Firm* — R. Scott Kimsey

(57) ABSTRACT

A tagged water-soluble polymer linked to a solid support is provided and includes a solid support optionally including a spacer sequence including one or more spacer monomer units attached to the solid support; and a water-soluble polymer covalently linked to the solid support or to the spacer sequence, the water-soluble polymer including a first cleavage segment including at least one monomer unit including a selectively cleavable link to the solid support or to the spacer sequence, where cleavage of the selectively cleavable link separates the water-soluble polymer from the solid support, a second segment including at least one monomer unit selected from a monomer unit linked to a reactive functionality able to be covalently coupled to a tag or linked to a tag, a third segment including one or more monomer units linked to a reactive functionality that can form a covalent bond with an analyte-binding species or an analyte, and optionally one or more spacer monomer units provided adjacent to any segment and/or between any two segments and/or within any one or more of the second segment and the third segment.

58 Claims, 9 Drawing Sheets

OTHER PUBLICATIONS

AM Adeyiga et al., "Advances in the Development of Lanthanide Macrocyclic Complexes as Luminescent Bio-Markers". Advanced Techniques in Analytical Cytology, Optical Diagnosis of Living Cells and Biofluids, T. Askura, D. L. Farkas, R. C. Leif, A. V. Priezzhev, and B. J. Tromberg Eds.; A. Katzir Series Editor, Progress Biomedical Optics Series Editor SPIE Proceedings Series, vol. 2678, pp. 212-220, 1996.

RC Leif and LM Vallarino, "Rare-Earth Chelates as Fluorescent Markers in Cell Separation and Analysis". ACS Symposium Series 464, Cell Separation Science and Technology, D. S. Kompala and P. W. Todd Editors, American Chemical Society, Washington, DC, pp. 41-58, 1991.

RB Merrifield, "Solid Phase Peptide Synthesis. I. The Synthesis of a Tetrapeptide". J. Am. Chem. Soc., 85, pp. 2149-2154, 1963.

P Lloyd-Williams et al., "Chemical Approaches to the Synthesis of Peptides and Proteins," CRC Press, Boca Raton, ISBN 0-8493-9142-3, p. 12-19, 1997.

GT Hermanson, Bioconjugate Techniques, Academic Press, ISBN0-12-342336-8, p. 150, 1996.

CC Barrett and DT Elmore, Amino Acids and Peptides, Cambridge University Press, Cambridge, ISNB 0 521 46827 2, p. 122-129, 1998.

L Pauling, The Nature of the Chemical Bond, Third Edition, Cornell University Press, Ithaca, p. 498, 1960.

T Strachan and AP Read, "Human Molecular Genetics 2nd ed", Wiley-Liss, Hoboken, ISBN 0-47133061-2, pp. 74-76, 1999.

JR Kettman, et al., "Classification and properties of 64 multiplexed microsphere sets", Cytometry 33, pp. 234-243, 1998.

L Stryer and RP Haugland, "Energy transfer: a spectroscopic ruler." Proc Natl Acad Sci USA 58, pp. 719, 1967.

Y Li and AN Glazer, "Design, synthesis, and Spectroscopic Properties of Peptide-Bridged Fluorescence Energy-Transfer Cassettes," Bioconjugate Chemistry 10, pp. 241-245 (1999).

AS Waggoner et al., "PE-CY5: A new fluorescent antibody label for three-color flow cytometry with a single laser." Ann. N.Y. Acad. Sci. 677: pp. 185-193, 1993.

E Gurr, "Synthetic Dyes in Biology, Medicine and Chemistry", Academic Press, SBN: 12309650-2, 1971.

J March, "Advanced Organic Chemistry Reactions, Mechanisms and Structure", 3rd Ed., J. Wiley & Sons, New York, pp. 361-363, 1985.

Bromme et al. "Enzyme-Substrate Interactions in the Hydrolysis of Peptide Substrates by Thermitase, Subtilisin BPN, and Proteinase K", Archives of Biochemistry and Biophysics, 244, pp. 439-446, 1986.

G Mezo et al. "Conjugation of Epitope Peptides with SH Group to Branched Chain Polymeric Polypeptides via Cys(Npys)", Bioconjugate Chemistry, 11, pp. 484-491, 2000.

RC Leif, "Methods for Preparing Sorted Cells as Monolayer Specimens". In Living Color, Protocols in Flow Cytometry and Cell Sorting, Eds. R. A. Diamond and S. DeMaggio, Springer, New York, ISBN 3-540-65149-7, pp. 592-619, 2000.

A Kallioniemi et al., "Detection and Mapping of Amplified DNA Sequences in Breast Cancer by Comparative Genomic Hybridization", Proc. Natl. Acad. Sci. USA. 91, pp. 2156-2160, 1994.

* cited by examiner

```
                        SEQUENCE LISTING

<160> NUMBER OF SEQ ID NOS: 2

<210> SEQ ID NO 1
<211> LENGTH: 19
<212> TYPE: PRT
<213> ORGANISM: Artificial
<220> FEATURE:
<223> OTHER INFORMATION: made with an amino acid synthesizer, sequence
      has a 3' endcap of PEGA [bis(2-acrylamidoprop-y-1-yl)
      poly(ethylene glycol) cross-linked dimethyl acrylamide and mono-2-
      acrylamidoprop-1-yl[2-aminoprop-1-yl] poly(ethylene

<400> SEQUENCE: 1

Ala Trp Ala Lys Ala Lys Ala Lys Ala Lys Ala Lys Pro Ala Pro Phe
1               5                   10                  15

Ala Ala Ala
```

```
<210> SEQ ID NO 2
<211> LENGTH: 30
<212> TYPE: DNA
<213> ORGANISM: Mus musculus

<400> SEQUENCE: 2
gggcttcaca acatctgtga tgtcagcagg                                          30
```

CONJUGATED POLYMER TAG COMPLEXES

CROSS-REFERENCE TO RELATED APPLICATIONS

This application claims priority to and is a Section 371 of International Application No. PCT/US00/27787 filed Oct. 7, 2000 published as International Publication No. WO 01/27625 A1 and to U.S. Provisional Patent Application No. 60/158,718 filed on Oct. 8, 1999, the disclosure of both of which are incorporated herein by reference in their entirety.

This invention was made with Government support under Small Business Technology Transfer Grant 5 R42 CA 73089 awarded by the National Institutes of Health, National Cancer Institute. The United States Government has certain rights in the invention.

BACKGROUND OF THE INVENTION

Definitions

To facilitate understanding of the method of this invention, the following definitions of terms used in this specification and claims are provided.

1. The term "lanthanide" is used to designate any of the trivalent lanthanide elements atomic number 57-71 as well as the lanthanide-like yttrium(III) and the actinide elements (atomic number 89-103).
2. Reactive functionality is used to mean a first atom or group capable of reacting with a second atom or group forming a covalent bond with it, as previously used in U.S. Pat. Nos. 5,373,093 and 5,696,240 to mean that both the first and second atom or group are capable of forming a covalent bond. These atom or groups include but are not limited to amines, azide, alcoholic hydroxyl, phenolic hydroxyl, aldehyde, carboxylic acid, carboxamide, halogen, isocyanate, isothiocyanate, mercapto and nitrile substituents. Functionalized alkyl, functionalized aryl-substituted alkyl, functionalized aryl, and functionalized alkyl-substituted aryl signify the respective alkyl, aryl-substituted alkyl, aryl, and alkyl-substituted aryl groups substituted with a reactive functionality.
3. Peptides are polymers that primarily are composed of monomer units that primarily are amino acids. The peptide monomer units are linked to one another by amide bonds.
4. Tag means the species or moiety that permits a molecule to be detected or to be affected non-destructively by a physical force.
5. Tagged means that a molecule that has formed a covalent bond with a tag.
6. Label means a tag that permits the detection of a molecule.
7. Labeled means that a molecule that has formed a covalent bond with a label.
8. Fluorescence means a process by which an electron of a molecule or ion that is in an electronic singlet state (a state in which the spins of all electrons are paired) absorbs the energy contained in a photon, with the result that this electron is elevated to a higher energy state, and subsequently an electron of this molecule or ion loses energy in the form of a photon and deactivates to a lower energy state. This process does not involve a change in the spin multiplicity of the molecule or ion.
9. Luminescence means all other processes by which an electron in a molecule or ion absorbs the energy contained in a photon, with the result that this electron is elevated to a higher energy state, and subsequently energy is lost from an electron in the form of a photon with the concurrent deactivation of this electron to a lower state. This process can involve a change of the spin multiplicity of the molecule or ion.
10. Absorbance means a process by which an electron in a molecule or ion absorbs the energy contained in a photon without the subsequent emission of a photon.
11. Optical-label means a tag capable of fluorescence, luminescence, or absorbance.
12. Luminescence-label means an optical-label that is capable of luminescence, such as a lanthanide macrocycle.
13. Fluorescence-label means an optical-label that is capable of fluorescence.
14. Absorbance-label means an optical-label that is capable of absorbance.
15. Other-label means a tag that is detectable by means other than fluorescence, luminescence or absorption of light, or that has a specific chemical or therapeutic activity. Other-labels include but are not limited to radioactive, paramagnetic, and sonic species.
16. Separation-tag means a tag that non-destructively affects the physical properties of molecules and molecular complexes. Separation-tags include magnetic, paramagnetic, charged, mass increasing, and density changing species.
17. Specific combining pair means a pair of molecules that form a stable complex without the formation of covalent bond(s) with one another.
18. Tagged-polymer means a polymer to which one or more tags are attached. These tags can be optical-labels, other-labels, or separation-tags.
19. Tagged-polymer-conjugate means a tagged-polymer where this polymer has formed a covalent bond with a molecular species other than itself or its tags.
20. Analyte means any compound of interest, naturally occurring or synthetic that is a member of a specific combining pair that is to be quantitated.
21. An analyte-binding species is the member of a specific combining pair that can form a stable complex with an analyte. These analyte-binding species include but are not limited to:
    a) an antibody or antibody fragment
       (i) Such antibodies or fragments may be defined to include polyclonal antibodies from any native source, and native or recombinant monoclonal antibodies of classes IgG, IgM, IgA, IgD, and IgE, hybrid derivatives, and fragments of antibodies including Fab, Fab' and F(ab')$_2$, humanized or human antibodies, recombinant or synthetic constructs containing the complementarity determining regions of an antibody, and the like. The methods useful for construction of all such antibodies are known to those of skill in the art.
    b) a polynucleotide, polynucleotide fragment, or an oligonucleotide
       (i) Such polynucleotides, polynucleotide fragments, or oligonucleotides include but are not limited to: deoxynucleic acids, DNAs; ribonucleic acids, RNAs; and peptide nucleic acids, PNAs.
    c) a lectin.
22. Tagged-analyte-binding species means an analyte-binding species to which is attached a tag. Since competitive assays employ tagged-analytes, when tagged-analyte species are employed for a competitive assay, tagged-analyte-species should be substituted for tagged-analyte-binding species.

23. Tagged-polymer-analyte-binding species conjugate means a polymer with one or more tags where this polymer has formed a covalent bond with an analyte-binding species.

FIELD OF THE INVENTION

This invention concerns: Composition of matter and a process for the preparation of tagged-poly-mer-analyte-binding species; and the use of tagged-polymer-analyte-binding species. Tags, labels, or dyes are covalently coupled to a polymeric substrate, which is covalently coupled to an analyte-binding species. The tags include luminescent, fluorescent, and absorbent labels or dyes; radioactive labels, paramagnetic labels; moieties that can increase the magnetic and or paramagnetic susceptibility, alter the electrical charge, alter the buoyant density, and increase the mass of a polymer-analyte-binding species conjugate.

The first citation in the text gives the first author's last name, year of the cited reference and the reference number preceded by Ref. in parenthesis. The (Ref. #) is always included in subsequent citations. Citations to books include the first page of the section of interest. United States patents are cited by number.

DESCRIPTION OF THE PRIOR ART

The sensitivity of fluorescence measurements for the analysis of biological samples is often limited by background signal due to autofluorescence or Raman scattering. For instance, a multilaboratory survey found the average autofluorescence of human lymphocytes to equal that of 657 fluorescein molecules (Schwartz et al., 1993), (Ref. 1).

An increase in the number of conventional organic fluorescent labels per targeted site results in quenching. For example, H. M. Shapiro, 1995 (Ref. 2) p. 91 describes one attempt at amplification of fluorescence signals by Tomas Hirshfeld et al., at Block Engineering, wherein several hundred fluorescein molecules were attached to a synthetic polymer, polyethylenimine, which was then conjugated with antibody. The method was not successful because fluorescence emission from fluorescein molecules was quenched due to the short nearest neighbor distances between fluorophores on the same polymer molecule. See H. M. Shapiro, 1995 (Ref. 2), p. 277. Presumably, this quenching is related to the partial overlap of the absorption and excitation spectra of the fluorescent molecules, J. R. Lakowicz, 1983 (Ref. 3), p. 305.

Haralambidis et al., (1990A) (Ref 4) described the synthesis of both peptide-oligodeoxyribonucleotide and polyamide-oligonucleotide carboxyfluorescein conjugates employing an Applied Bio-systems Inc. automated DNA synthesizer. The peptide or polyamide was first assembled on a solid support. The terminal amino group was converted to an amide by reaction with an α,ω-hydroxycarboxylic acid derivative. The free hydroxyl group was then esterified with a phosphoramidite and the peptide- or polyamide-substituted polynucleotide was subsequently assembled by sequential reaction with methyl N,N-diisopropyl nucleoside phosphoramidites. Protected lysine residues were included in both the peptide and the polyamide to provide primary amino functionalities suitable for conjugation to the fluorescent species. In a subsequent paper, Haralambidis et al. (1990B) (Ref. 5) reported labeling the polyamide-linked oligonucleotide probes with multiple carboxyfluorescein units, after deprotection of the primary amino groups of the lysine residues. However, the resulting oligonucleotides "carrying multiple carboxyfluorescein labels gave low levels of fluorescence due to quenching" (Ref. 5). These authors reported that "The amount of fluorescence per fluorescein moiety is 20 times less than that of carboxyfluorescein in the conjugates with ten lysines", even when the lysine residues were separated by two or four spacers.

Multiple fluorescent-labels have been bonded to dextrans in order to maximize the fluorescence emission. Numerous fluorescent dextrans are commercially available. R. P. Haugland, 1996 (Ref. 6) p. 351. Fluorescent dextrans consist of soluble dextrans (that is dextrans with molecular masses of 3,000, 10,000, 40,000, 70,000, 500,000, and 2,000,000 daltons) conjugated with various fluorescent species such as fluorescein, dansyl, rhodamine, and TEXAS RED®. The degrees of substitution in these fluorescent dextrans are 0.5-2 fluorescent species per dextran of 10,000 daltons, 2-4 fluorescent species per dextran of 40,000 daltons, 3-6 fluorescent species per dextran of 70,000 daltons. Conjugated dextrans are also available as so-called "lysine-fixable", that is, they have incorporated lysine residues which can be used for further reaction, such as covalent attachment of antibody molecules. Fluorescein isothiocyanate (FITC) derivatives of dextran and poly-L-lysine, with degrees of substitution ranging from 0.003 to 0.020 molecules of FITC per molecule of glucose and from 0.003 to 0.02 molecule of FITC per molecule of glucose, are commercially available from sources, such as SIGMA-ALDRICH®, 2000-2001 (Ref. 7) p. 428.

Siiman et al. U.S. Pat. No. 5,891,741 (Ref. 8) have described increasing the fluorescence of individual antibody molecules by conjugation with a dextran crosslinked, ligand-(phycobiliprotein or tandem dye) conjugates containing up to twenty five phycobiliprotein or tandem fluorescent species per dextran molecule. U.S. Pat. No. 5,891,741 describes a method for preparing the antibody-aminodextran-phycobiliprotein conjugates.

This method comprises the steps of:
(a) activating the antibody with iminothiolane, then purifying the activated antibody;
(b) activating the phycobiliprotein with iminothiolane, then purifying the activated phycobiliprotein;
(c) combining the activated and purified antibody and phycobiliprotein;
(d) activating the aminodextran with sulfo-SMCC, then purifying the activated aminodextran;
(e) mixing all activated components together for about 16-24 hours; and
(f) purifying the mixture into its components, preferably by size exclusion chromatography.

Although U.S. Pat. No. 5,891,741 teaches a method to increase the fluorescence of an antibody, it differs from the invention described below in that:

1) it does not describe achieving a high concentration of fluorescent labels.
2) it does not provided a means to control the spatial organization of the labels.
3) more than one antibody molecule can be attached to an aminodextran molecule. And
4) the molecular weight of the aminodextran conjugate without the antibody is much larger than that of any of the following: an IgG antibody (MW, 160,000 daltons), most other commercial analytes, analyte-binding species, conventionally conjugated analyte-binding species, conventionally conjugated analytes, analyte-binding species conjugated with the tagged peptides described in this invention, and analytes conjugated with the tagged peptides described in this invention. Thus, the reaction rate of the analyte with its combining member, the aminodextran conjugate, will be significantly slowed by being conjugated with the aminodextran.

Peterson et al. 1998 (Ref. 9) have reported on the Merrifield synthesis of support-bound peptides that are substrates for cathepsin B and cathepsin D. These authors stated that, "The solubility properties of the PEGA support allow enzymatic permeability in an aqueous environment". The authors described PEGA as "bis(2-acrylamidoprop-y-1-yl) poly(ethylene glycol) cross-linked dimethyl acrylamide and mono-2-acrylamidoprop-1-yl[2-aminoprop-1-yl] poly(ethylene glycol) (800)". Enzymatic cleavage liberates the peptide that is N-terminal to the cleavage site. The cathepsins were chosen because they are lysosomal endoproteases. The authors stated, "insertion of a peptide substrafe between a radiolabeled chelate and its targeting moiety (e.g., an antibody) may lead to expedited clearance of undesirable radioactivity from the liver during radioimmunotherapy and imaging". In a subsequent publication, Peterson et al. 1999 (Ref. 10), these authors reported on the synthesis of peptides that included a site for hydrolytic cleavage by cathepsins B and D and had a DOTA group attached by a peptide bond to the N terminal amino acid and a p-isothiocyanatophenylalanine attached by a peptide bond to the C terminal amino acid. DOTA, which can bind the radioactive ion $^{90}Y$, is an abbreviation for 1.4,7, 10-tetraazacyclododecane-N,N',N'',N'''-tetraacetic acid. The p-isothiocyanatophenylalanine can be bound to the lysines of proteins including antibodies.

These peptide conjugates: 1) are incapable of fluorescence or luminescence 2) only bind one chelating moiety; 3) are not bound to the protein via their N terminus, and 4) their mode of use does not involve enzymatic cleavage from the support.

Takalo et al. 1994 (Ref. 11) have reported that they were able to label IgG with up to 25 europium(III) chelates per rabbit IgG and "increasing the amount of chelates in a protein does not have any major effect on quantum yield." They did note, "Accordingly, the total luminescence can be increased by more efficient labeling as long as immunoreactivity is retained.". These authors also stated, "The most strongly reactive intermediate, dichlorotriazinyl activated chelate, may also cause decreased affinities when used in high excess conditions." Takalo et al's disclosed chemical reactions employed for the attachment of the fluorescent or luminescent moieties are not limited to conditions that permit the retention of biological activity or the retention of the chemical integrity of the biomolecule.

Lamture et al. 1995 (Ref. 12) have conjugated 4-(iodoacetamindo)-2,6-dimethylpyridine dicarboxylate, IADP to polylysines. This polymeric conjugate of polylysine and IADP binds Tb(III) ions with very high affinity, has been coupled to proteins, and very efficiently enhances their luminescence. These authors state, "It has the added advantage that multiple luminescent Tb(III)-DPA complexes are present in each labeled protein, even if only one site on the protein is modified with the polymer, so that the molar luminescence intensity is brighter than that of conventional monomeric fluorophores." Lamture et al. reported that attachment of the DPA to poly-L-lysine with nominal average molecular weight of 26,000 results in greatly increased resistance to EDTA. They state, These results suggest that Tb-PLDS complexes (Tb(III)-DPA poly-L-lysine conjugates) are approximately 50,000 times more stable than Tb-EDTA."

The conjugation of bovine serum albumin, BSA, to Tb-PL DS complexes was described. The unreacted lysines of the DPA poly-L-lysine conjugates were reacted with N-hydroxysullosuccinimide in the presence of 1-(3-dimethylamino) propyl)-3-ethylcarbodiimide hydrochloride, EDC. After the lysines were activated, BSA was added. Similar conditions were employed to conjugate ovalbumin, protein A, and avidin. Coomassie-Blue stained Sodium DodecylSulfate-polyacrylamide electrophoresis, SDS-PAGE, of the BSA conjugates showed the presence of a continuum of molecular weights starting with BSA monomers. The distribution of terbium luminescence on the gels was not mentioned or reported. In the case of the avidin conjugates, Lamture et al. stated that it would be possible to obtain better results "by protecting lysines essential for biotin binding during the labeling reaction." These authors employed only one type of reactive functionality, the epsilon amino group of lysine, rather than the two or more reactive functionalities, as specified in the present invention. All of the chemistries occurred in the liquid phase, rather than with the use of a support as specified in the present invention.

Kwiatkowski et al. 1994 (Ref. 13) have compared the emissions from 20 base long oligonucleotides that additionally included "either 1, 2, 5, 10, or 20 europium chelate-modified nucleotides". These authors stated, "that the direct fluorescence, per europium ion, is independent of the number of chelates present in each oligonucleotide." They concluded that the emission intensity could be increased in the proportion of the number of chelates added. The oligonucleotides were labeled by chemically adding deoxyuridine and deoxycytidine derivatives onto either the 5'- or the 3'-end of oligonucleotides. Addition to the 3'-end permitted the use of standard DNA supports. The deprotection steps included 0.1M sodium hydroxide and "standard ammonia deprotection". These steps are inconsistent with the maintenance of biological function of proteins, such as antibodies. The lanthanide binding functionality is directly attached to the analyte-binding species.

Salo et al. 1998 (Ref. 14) have synthesized disulfide linkers for the solid phase synthesis of oligonucleotides. The disulfide linker N-[6-[(4,4'-Dimethoxytrityl)oxy]-12,13dithiahexadecanoyl] was attached to amino-modified TENTA-GEL™. "The protected oligonucleotides were assembled on an Applied Biosystems 392 DNA synthesizer" using phosphamidites. The first two nucleotides were $N^4$-(6-aminohexyl)-2'-deoxycytidine, which were both labeled with either 5-(dimethylamino)-I-naphthalenesulfonyl chloride or a dichlorotriazine derivative of a photoluminescent europium (III) chelate. The europium(III) labeled chelate 18 mer oligodeoxyribonucleotide was cleaved from the solid by dithiothreitol and was used successfully for a sandwich hybridization.

The methodology of the present invention differs from Salo et al. (Ref. 14) because 1) the species produced by these authors could not be stored for subsequent attachment of an oligonucleotide without the use of specialized, expensive instrumentation. 2) Their methodology was unsuited and was not directed to proteins or other analyte-binding species. 3) Enzymes were not used for the cleavage of their oligonucleotides from the support, and 4) No mention was made of the possibility of employing the disclosed technology with peptides or PNAs.

Inorganic phosphor particles (D. A. Zarling et al. U.S. Pat. No. 5,736,410, 1998 (Ref. 15) have been used as multiple labels or tags. However, the absorption spectrum of these particles is narrow, resulting in the preferred method of illumination being two photon absorption of infrared laser light. The use of these particles is limited by nonspecific binding; furthermore, the total binding of rigid particles to solid substrates and cells is limited to a small contact zone.

Vallarino and Leif have reported in U.S. Pat. No. 5,373, 093, 1994 (Ref. 16) and its Continuation-In-Part U.S. Pat. No. 5,696,240, 1997 (Ref. 17) on symmetrically di-functionalized water soluble macrocyclic complexes of rare-earth, actinide and yttrium ions. A di-functionalized macrocyclic complex is represented by the schematic Formula I:

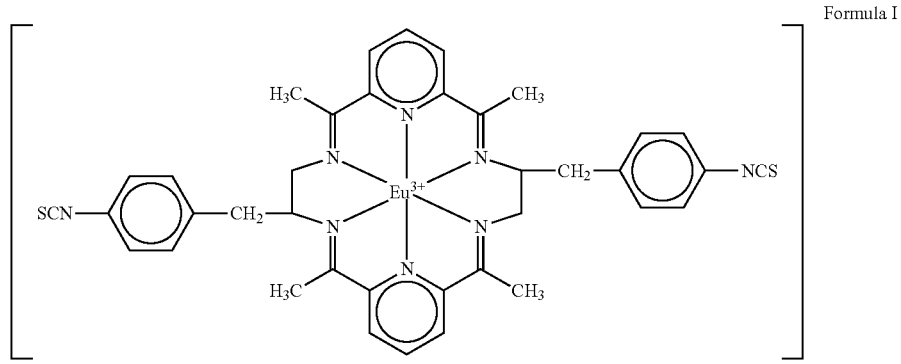

Formula I

Formula I is the di-isothiocyanate derivative having the structure shown in column 10 of U.S. Pat. No. 5,373,093. Specifically, it is one of the isomers of the cationic europium macrocyclic moiety containing a 4-isothiocyanate-benzyl-substituent on each of the aliphatic side-chains. The molecular formula of the moiety is $C_{38}H_{36}N_8S_2Eu$. Its trichloride was used in liquid phase coupling reactions of this application.

In U.S. Pat. No. 5,696,240, asymmetrically mono-functionalized water soluble macrocyclic complexes of rare-earth, actinide and yttrium ions are described. A mono-functionalized macrocyclic complex is represented by the schematic Formula II:

Formula II is the mono-isothiocyanate derivative having the structure shown in Claim 13 of U.S. Pat. No. 5,696,240. Specifically, it is the cationic terbium macrocyclic moiety containing a 4-isothiocyanate-benzyl-substituent on one of the aliphatic side-chains. The molecular formula of the moiety is $C_{30}H_{31}N_7STb$. Its trichloride was used in solid phase coupling reactions of this application.

The following abbreviations will be used to describe molecular structures related to those shown in Formula I and in Formula II. Any and all of the metal ions selected from the group consisting of a lanthanide having atomic number 57-71, an actinide having atomic number 89-103 and yttrium (III)

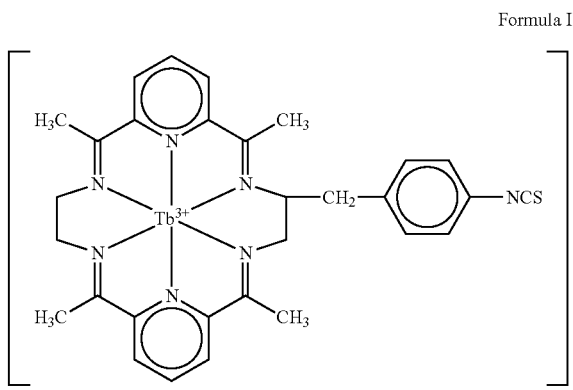

Formula II having atomic number 39 will have M as their abbreviation. Specific metal ions will be given as their standard chemical symbols. The mono-functionalized and di-functionalized macrocyclic complexes will be abbreviated respectively as "Mac-mono" and "Mac-di". The term Mac without the mono or di prefix will include both the mono-functionalized and di-functionalized macrocyclic complexes (Mac-mono and Mac-di). When a specific peripheral pendant substituent having at least one reactive site (reactive functionality) is specified, its abbreviation will be given as a suffix. Thus, the compound shown in Formula I is abbreviated as EuMac-di-NCS. The compound shown in Formula II is abbreviated as TbMac-mono-NCS. The generic term, M-Mac, will refer to any and all of the macrocyclic species covered by U.S. Pat. Nos. 5,373,093 and 5,696,240.

U.S. Pat. No. 5,373,093 and its Continuation-In-Part U.S. Pat. No. 5,696,240 teach the structures, synthesis and use of functionalized water soluble macrocyclic complexes of lanthanide, actinide and yttrium ions. "Symmetrically di-functionalized water soluble macrocyclic complexes of lanthanide, actinide and yttrium ions were obtained by metal templated, Schiff-base, cyclic condensation of: (1) a functionalized 1,2-diaminoethane and a dicarbonyl compound selected from the group consisting, of 2,6-dicarbonylpyridine, 2,6-diformylpyridine, 2,5-dicarbonylfuran, 2,5-diformylfuran, 2,5-dicarbonyl-thiophene and 2,5-di formylthiophene; or (2) 1,2-diaminoethane and a ring-substituted heterocyclic dicarbonyl compound selected from a group consisting of substituted 2,6-dicarbonylpyridine, substituted 2,6-diformylpyridine, substituted 2,5-dicarbonylfuran, substituted 2,5-diformylfuran; substituted 2,5-dicarbonyl thiophene, and substituted 2,5-diformylthiophene."

U.S. Pat. No. 5,696,240 teaches the structures, synthesis and use of "asymmetrically functionalized water soluble macrocyclic complexes of the lanthanide, actinide and yttrium ions were obtained by metal templated, Schiff-base, cyclic condensation of appropriately substituted diamine and dicarbonyl precursors, with such precursors contributing two heteroaromatic moieties (pyridine, furan, thiophene, or a combination thereof) to the resulting macrocyclic structure. The coordination complexes thus formed are kinetically stable in dilute aqueous solution. They are further reacted, or coupled, through a substituent on the 1,2-diaminoethane or on the pyridine, furan, or thiophene moieties, to one of the following: proteinacious materials, polysaccharides, polynucleotides, peptide nucleic acids, other biologically compatible macromolecules or bridging molecules, which can be further reacted or coupled to the above mentioned substrates. These macrocyclic complexes are suitable in the preparation of reporter molecules and for magnetic resonance, radiation imaging and radiation therapy."

Leif et al. 1994 (Ref. 18) described the use of symmetrically di-isothiocyanate-functionalized macrocyclic complexes of a lanthanide(III) ion, which served as the light-emitting center. The isothiocyanate functionalities allow covalent coupling of the lanthanide(III) macrocycles to a biosubstrate. The Eu(III) and Tb(III) complexes possess a set of properties—water solubility, inertness to metal release over a wide pH range, ligand-sensitized narrow-band luminescence, large Stokes' shift, and long excited-state lifetime—that provide ease of staining as well as maximum signal with minimum interference from background autofluorescence. These authors stated, "The results with the $^5D_0 \rightarrow {}^7F_2$ (610-625 nm) Eu(III) transition, which is the major signal source, show that the luminescence of the EuMac-enhancer system is highly dependent upon the choice of both buffer and solvent. The emission intensity increases dramatically in the absence of those buffers that contain anions, such as carbonate, capable of competing with the β-diketonate enhancers as ligands for Eu(III). The emission intensity also increases greatly in the less hydroxylic solvents. However, vibrational deactivation by interaction with the —OH groups of solvent molecules can not be solely responsible for the energy loss, since substitution of $D_2O$ for $H_2O$ as the solvent had been reported (Ref. 19) to result only in a three-fold increase of the EuMac excited-state lifetime."

The low quantum yield of the EuMac in aqueous medium probably precludes its use as an optical-label for the observation and measurements of live cells (Ref. 18). However, this complex can be used in conventional fluorescence (luminescence) microscopy, providing the cells are mounted in an appropriate nonaqueous medium or in an aqueous medium to which has been added a micellar solution which contains a second lanthanide ion, Bromm et al. 1999 (Ref. 20) and Quagliano et al. 2000 (Ref. 21). In the case of a nonaqueous medium (Adeyiga et al. 1996 (Ref. 22), either ethyleneglycol replaces glycerol, which is conventionally employed as the mounting medium, or a permanent mounting medium, such as ACCU-MOUNT 60™ (Stephens Scientific, Riverdale, N.J.), is employed. A dry specimen can be either observed and/or quantitated. Clinical diagnostic and other uses of the EuMac as optical-label, such as immunodiagnostics, are feasible providing the measurements are performed in a nonaqueous solvent such as ethanol or the sample is dry.

Adeyiga et al. 1996 (Ref 22) described: 1) Protocols for the coupling of NCS-substituted Eu-macrocycles to proteins and for the mounting on microscope slides of particles labeled with luminescent Eu-macrocycles. The emission/excitation spectra of the dried, slide-mounted particles were investigated. 2) The synthesis of lanthanide-macrocycles having a single peripheral functionality, as well as the structure and properties of these complexes was described.

The mono-isothiocyanate functionalized macrocyclic complex of Tb(III) (Ref. 17), which is illustrated in Formula II of this application, and the di-substituted analog (Ref. 16), which is illustrated in Formula I of this application, fulfill all fundamental requirements of a luminescent marker for cell imaging and solid-phase immunoassays. These complexes do not release the lanthanide ion even in very dilute aqueous solution and the presence of competing ligands. Since the lanthanide macrocyclic complexes are formed around the lanthanide ions during the lanthanide-templated synthesis, rather than by binding the lanthanide ions to preformed macrocyclic ligands, these species are kinetically stabilized (Ref. 23) and will not dissociate under the experimental conditions employed for the formation of antigen-antibody complexes or for the hybridization of an oligonucleotide to DNA or RNA. As is well known, the lanthanide(III) ions in the M-Mac can bind two enhancers, one on each of the opposite sides of the macrocycle (Ref. 23). This binding permits an efficient energy transfer from the absorber—the enhancer—to the lanthanide emitter. The enhancers also shield the excited lanthanide ion from direct contact with water, which ordinarily would quench the luminescence by vibronic interaction.

SUMMARY OF THE INVENTION

In accordance with this invention, there is provided a tagged, water-soluble, polymer linked to a solid support and selectively cleavable therefrom, such polymer comprising a cleavage segment of known composition, form, and sequence within which cleavage of a bond separates the polymer from the support; a second segment of known composition, and sequence comprising one or more tagged monomer units; a third segment comprising one or more monomer units with a reactive functionality that can form a covalent bond with an analyte-binding species; and zero or more spacer monomer units, wherein at least one of the tagged monomer units is linked to a moiety that is an optical-label, an other-label or a separation-tag. These tags can serve as a luminescent, fluorescent, and/or absorbent label; or as an other-label, which serves as a radioactive, paramagnetic, or sonic label; or as a separation-tag that non-destructively affects a physical property, such as magnetic susceptibility, electrophoretic mobility, buoyant density or mass, of a specific combining pair or species of which the analyte is a part. Emission of light can take place by a luminescence or fluorescence mechanism as defined. The absorption and/or emission of light by the optical-label can occur in the range from 200 to 1,400 nanometers. Other-labels can also be radioactive, capable of being transformed into radioactive substances, and/or detectable by radiological means including but not limited to radioactive emissions and/or magnetic resonance imaging. The binding of multiple separation-tags, non-destructively affecting a physical property can sufficiently change such property to permit the separation of a specific combining pair or species of which the analyte is a part. Any tag can serve multiple purposes. For example, lanthanides can be luminescent, paramagnetic, as well as radioactive; lanthanides can change the charge, buoyant density and mass of tagged-polymer-analyte-binding species.

The polymer according, to the invention can be represented by Formula III:

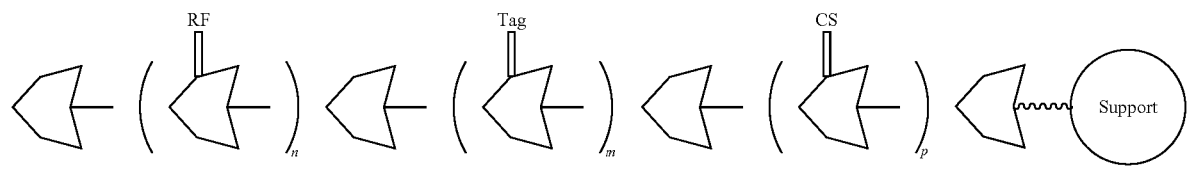

Formula III in which each left pointing broad-arrow shape represents a monomer unit; RF represents a reactive functionality linked to a monomer unit; Tag independently at each occurrence represents an optical-label, or other-label, or separation-tag linked to a monomer unit; CS represents at least one monomer unit constituting the cleavable link to the support shown by the circular shape at the right; broad-arrow shapes without other indication represent spacer monomer units, n is a number from 1 to 10, m is a number from 1 to 1,000 and p is a number from 1 to 25.

The first monomer unit of the polymer is covalently bound to the support or to another polymer attached to the support. The number of spacer monomers is governed by cost and depends on their position in the polymer; it can reasonably range from 0 to (20×m)+100. Spacer monomers can be placed within groups of both tag-bearing and reactive functionality-bearing monomers. From 1 to 10 types of tags can be linked to monomer units.

The molecular weight of the polymer of this invention is at least that of the essential three monomer units defined above. There is in principle no upper limit except the practical consideration that the added cost of more monomer units be justified by added benefits of their presence. Hence the polymer of the invention preferably includes from 3 to 1000 monomer units and more preferably has a molecular weight in the range from 1000 to 100,000 daltons. The polymer of the invention, therefore, can have bound one to approximately 1,000 tags; it can be selectively cleaved from the support by enzymatic as well as other techniques that do not destroy the tags; it can be covalently bound to an analyte-binding species or an analyte; and it can be so cleaved after being bound to this analyte-binding species or analyte.

The linkage of the polymer to a solid support permits monomer units to be added in a specific order, suitably by an iterative synthesis. Thus, in the case of peptides or any other type of polymer in which specific monomer sequences permit tags to have a specified relative geometric position in space, these geometric relative positions can be controlled. This eliminates the often very difficult synthetic chemistry problem of synthesizing a direct bond between two molecules and also providing a reactive functionality that can couple this dimer to an analyte-binding species. Thus, a pair of molecules where one transfers energy to the other can be linked together by each separately forming covalent bonds with monomers that are part of the same polymer or monomers with appropriate optical-labels being directly incorporated into the polymer. A further advantage is the selective cleavage of the polymer from a solid support, which provides the ability to work with the polymer attached to solid support or in solution, as desired. Selective cleavage means the ability to sever the linkage between the polymer and the solid support, in preference to severing covalent linkages of monomer units within the polymer or linkages of tag moieties to monomer units, or linkages between the polymer and analyte-binding species or analyte. The formation of a complex between the analyte-binding species and an analyte where one, or the other, or both are an optical-labeled-polymer-conjugate permits the detection and/or quantitation of this analyte by the interaction of light with the light absorbing and light emitting species of the water-soluble polymer; or the detection or use of other-labels; or the separation of this analyte or specific combining pair by physical means. After cleavage of the tagged-polymer-conjugate from a support, either the detection and/or quantitation of an analyte and/or the separation of an analyte or specific combining pair by physical means can be performed in solution. Yet another possible use is the directed delivery of the tags to cells for therapeutic purposes.

This invention addresses the deficiencies in the prior art by providing a series of peptides or other polymers that contain covalently bound tags, a reactive functionality for coupling to an analyte-binding species, and a cleavable linkage to a solid support. Procedures for producing tagged-polymer-analyte-binding species are also described. The possible tags include optical-labels, other-labels, and separation-tags while both these tags and the analyte-binding species may be labile, any potential danger of decomposition under the conditions required for the chemical reactions involved in the sequential solid-phase synthesis of polymers and in the cleavage of these polymers from the solid support is minimized according to the invention. The preparation of tagged-analyte-binding species is simplified for the end user according to the invention, when the analyte is bound in the solid phase to a pre-manufactured tag and then the tagged-analyte-binding species is selectively cleaved from the support with its intact tag(s) attached.

This invention also includes a water-soluble polymer linked to a solid support and selectively cleavable therefrom, comprising closest to the support a cleavage segment, of known composition and sequence made up of at least one monomer unit; a second segment of known composition and sequence separated from the support by at least the cleavage section and including one or more monomer units each of which is linked to either a reactive functionality able to be covalently coupled to a tag or linked to a tag, and a third segment of known composition and sequence separated from the support by at least the cleavage section and including at least one monomer unit linked to a reactive functionality, capable of forming a covalent bond with an analyte-binding species or an analyte; from 1 to 10 types of tags can be linked to the monomer units.

Such a polymer can be represented by the schematic Formula IV:

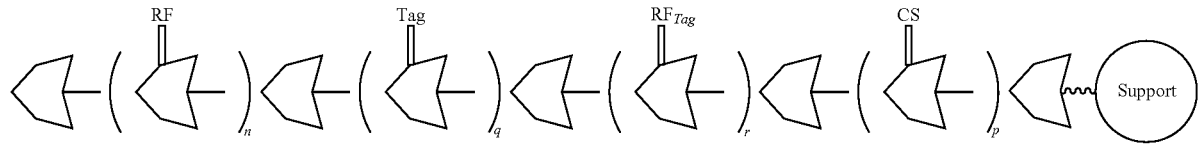

Formula IV wherein each left pointing broad-arrow shape represents a monomer unit; RF independently represents a reactive functionality linked to a monomer unit and serving to bind to an analyte-binding species; $RF_{tag}$ independently at each occurrence represents a reactive functionality able to be covalently coupled to a tag; Tag independently at each occurrence represents an optical-label, or other-label, or separation-tag linked to a monomer unit; CS represents at least one monomer unit constituting the cleavable link to the support shown by the circular shape at the right; broad-arrow shapes without other indication represent spacer monomer units, which need not be present; n is a number from 1 to 10; r is a number from 0 to 1,000; q is a number from 0 to 1,000, provided that the sum of r and q is a number from 1 to 1,000; and p is a number from 1 to 25.

DETAILED DESCRIPTION OF THE INVENTION

Figure 1:
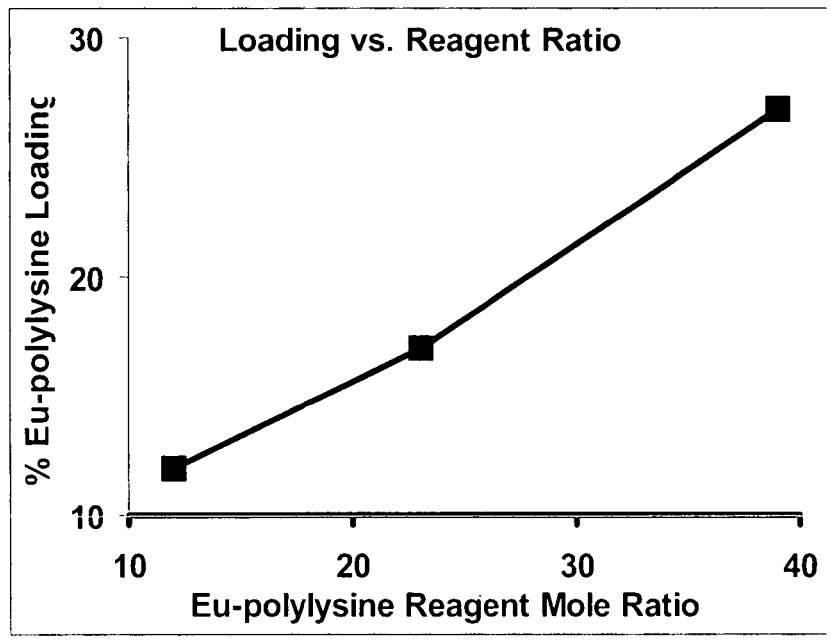
FIG. 1. Plot of the average EuMac-to-polylysine loading in coupled polylysine versus the EuMac-di-NCS-to-polylysine mole ratio used in the coupling reaction. The loading is expressed as percentage of EuMac-coupled lysine residues.

Three ways to covalently bind a tag with special desired properties to a polymer back-bone are: 1) Synthesize monomers which incorporate the tag(s); if necessary, each tag can be chemically protected by an appropriate protecting group. The tagged monomers are then incorporated into the polymer in the desired order as the polymer is synthesized. An example of a commercially available (ANASPEC, Product #23357, 2000-2001) tagged monomer is Fmoc-Lys(Fluorescein)-OH. 2) Sequentially react a growing polymer, after the addition of a functionalized monomer, with a species capable of forming a bond with the reactive functionality of said monomer, with the result of producing a tagged monomer already incorporated into the polymer. 3) Synthesize a polymer containing various monomer units with different reactive functionalities, and react these with species specific for each functionality to produce tagged monomer units. These reactions can occur after all of the monomers have been incorporated into the polymer, with the advantage that the tags are never exposed to the conditions required for the reactions employed in the polymer synthesis. If the polymer is synthesized on a solid support, there is still the possibility that the tags may be affected by the often harsh conditions required for the cleavage of the polymer from the support. This potential problem is further exacerbated if the binding of the analyte-binding species to the tagged-polymer is carried out, as often desirable, while the polymer is still bound to the solid support. This invention therefore includes a very mild enzyme-based selective cleavage of the polymer from the solid support, carried out under conditions that do not affect either the tails or the analyte-binding species. In fact, a protein (an antibody) has been demonstrated to withstand the cleavage step. This invention has the further advantages of permitting control of the location of the tags relative to each other, and of requiring reaction with only one site on the analyte-binding species, thus minimizing interference with its biological function.

A more detailed description of the elements of the tagged-polymer-analyte-binding species and their individual and combined utility follows.

Water-Soluble Tagged-Polymer Linked to a Solid Support
    Solid Support

The solid support is any water-insoluble solid, organic or inorganic, that can be linked to a polymer comprising at least one tagged monomer unit, at least one monomer unit bearing a reactive functionality, and at least one monomer unit that can be selectively cleaved from the support, and when desired at least one spacer monomer unit.

The criteria for the use of such a support, first disclosed in R. B. Merrifield's pioneer publication (Ref. 24) on solid phase peptide synthesis, are still applicable here. This technology is extensively described in P. Lloyd-Williams et al. 1997 (Ref. 25), which is incorporated by reference.

Preferably the support is a swellable bead with pendant hydrophilic polymer side chains having a wet particle size of about 10 to 1,000 microns, functionalized so as to react with the terminal monomer of the cleavage segment. In the case of a peptide cleavage segment linked to the support through a terminal carboxyl group, the bead is functionalized with a group reactive therewith, such as an amino group or a halomethyl group, and in the case of a polynucleotide, an aliphatic hydroxyl. The optimum size of the beads will depend on the exact circumstances of their utilization including cost. Presently, it is beads in the range of 150-300 um.

Suitable solid supports are known in the art and many are commercially available. Examples are listed in the Polymer Laboratories Catalog 2000 is incorporated herein by reference. The supports can be hydrophobic or hydrophilic. When the support is hydrophobic, the polymer is bonded to the support in the presence of an organic solvent that swells the support to a multiple of its dry volume. Hydrophobic supports include: cross-linked polystyrene. chloromethyl-substituted polystyrene, aminomethyl-substituted polystyrene with controlled degree of crosslinking as with approximately 1% divinylbenzene, and polyamide. A hydrophilic support has the advantage that an organic solvent is not required and the polymer can be bonded to the support in the presence of water. Hydrophilic polymers such as polyethylene glycol can be grafted to hydrophobic supports such as polystyrene. In the resulting structure, the hydrophobic component of the support provides mechanical stability while the hydrophilic component increases the number of sites that can be employed for polymer synthesis, which is proportional to the number of polymers that can be synthesized. Hydrophilic monomer units of any desired molecular size can serve to increase the length of the cleavable link of the polymer of the invention to the solid support. This increased access to these polymers facilitates the addition of monomer units, the reactions with other molecules, and in particular the interaction of an enzyme with its substrate in selectively cleaving the polymer of the invention from the support. Other suitable hydrophilic supports include polyvinyl alcohol bound to acrylic polymers and, in general, any hydrophilic polymer that does not interfere with the chemical reactions of the Merrifield synthesis, and that permits an amino acid or other monomer to be bound to the support via a cleavable covalent link and to be cleaved therefrom. These supports are described in Lloyd-Williams et al. 1997 (Ref. 25) Chapter 2, Solid-Phase Peptide Synthesis, 2.1 The Solid Support p 19.

Preferably, the support is a hydrophilic bead with pendant hydrophilic polymer side chains that has an exceptionally high swell in all solvents including water, and can allow large macromolecules, such as enzymes, to permeate the particles. The end of the polymer side chains distal to the bead should be a reactive functionality, reacting with a reactive functionality of the monomer reactant, in the way that an amino group linked to the support reacts with a carboxyl functionality of an amino acid in forming a peptide.

Water Soluble Tagged-Polymers

Polymers provided according to this invention include all structures available through iterative synthesis including polypeptides; nucleic acids, oligosaccharides; and in general any linear polymer containing tagged monomer units and terminating at one end with functional group(s) suitable for binding to a solid support; and while at the other end a functional group is available that is suitable for binding to it another monomer including a monomer with a reactive functionality that can form a covalent bond with a member of an analyte-combining pair. A variant on this is to form dendrimeric structures which include the polymer of the invention within a branched polymeric structure.

Tagged monomer units in the polymer according to this invention are monomer units that include an optical-label, other-label, or a separating-tag. Monomer units with a reactive functionality covalently bind with a member of a specific combining pair, usually the analyte-binding species, while not reacting with the species that constitute or form tags on the tagged monomers. Spacer monomer units are those that lack either a tag or a reactive functionality. Many types of monomer units are available. Preference is given to those that can participate in iterative syntheses of polymers according to the invention in which the kind, number, and order of the monomer units follows a predetermined pattern, and for which the spatial geometric orientation of the resulting polymers can be ascertained.

As pioneered by Merrifield (Ref. 24), such iterative syntheses are preferably carried out with the first monomer unit linked to a solid support, either directly, or through one or more monomer units not intended to be part of the polymer according to the invention; the subsequent monomer units are then successively linked to the first monomer unit in stepwise fashion, until the predetermined kind and number of monomer units have been linked in the desired order, whereupon the polymer so formed is selectively cleaved from the support.

When the polymer according to the invention includes a polypeptide, the monomer units comprise aminocarboxylic acid units, amino acids. The polypeptide according to the invention can be represented by Formula V:

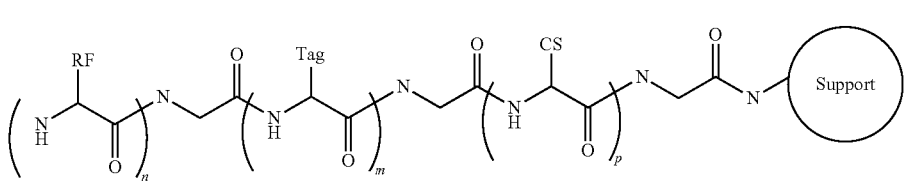

Formaula V

In Formula V, the free amino group end of the peptide is at the left and the carboxylic acid end is at the right; the solid support is shown by the circular shape at the far right. RF represents a reactive functionality of an amino acid; Tag independently at each occurrence represents an optical-label, other-label, or separation-tag covalently bound to an amino acid; CS represents a cleavable link to the support. Spacer amino acids, which have unreactive side chains, are shown as lacking a side chain. n is a number from 1 to 10, m is a number from 1 to 1,000, and p is a number from 1 to 25.

From 1 to 10 types of tags can be linked to the amino acid monomer units. At least one amino acid with a reactive functionality is required to bond to one analyte-binding species.

The molecular weight of the polymer of this invention is at least that of the essential three monomer units defined above. There is in principle no upper limit except the practical consideration that the added cost of more monomer units be justified by added benefits of their presence. Hence the polymer of the invention preferably includes from 3 to 1000 monomer units and more preferably has a molecular weight in the range from 1000 to 100,000 daltons.

The first amino acid in the polymer sequence according to the invention is covalently linked to the support directly or through a group not part of the polymer of the invention attached to the support. The number of spacer amino acids is governed by a balance between the cost of synthesis, which increases with the number of spacers, and the optimal number of spacers required to provide the desired three-dimensional conformation of the peptide. The number of spacer amino acids can reasonably range from 0 to (20×m)+100. Spacer amino acids can be intercalated as appropriate within or between groups of both tag-bearing and reactive functionality-bearing amino acids.

The amino acids functioning as monomer units in the polymer according to the invention can be either naturally occurring or synthetic; they can be alpha amino acids or other compounds that contain at least one amino group and at least one carboxyl group. The amino acids suitable for coupling to a tag or forming a covalent linkage to an analyte-binding species are N-terminal amino acids with free amino groups and those amino acids that have side chains carrying reactive functionalities such as: amino groups, carboxyl groups, hydroxyl groups, and mercapto groups. The chemistry of these and other coupling reactions is described in Hermanson, 1996 (Ref. 26) which is incorporated by reference. All naturally occurring alpha amino acids except glycine are in the L configuration and have synthetic D counterparts. Many synthetic amino acids, both non-functionalized or functionalized, have been synthesized as racemates as well as the L and D forms and can be incorporated into peptides by the method of iterative synthesis. Some of these are described in Barrett and D. T. Elmore, 1998 (Ref. 27) which is incorporated herein by reference. Numerous 9-Fluorenylmethyloxycarbonyl (Fmoc) and t-Butoxycarbonyl (Boc) amino acids including those with protected reactive functionalities are commercially available. Examples are listed in the ANASPEC Catalog 2000-2001, which is incorporated herein by reference. A reactive functionality can be introduced into a non-functionalized and/or functionalized amino acid by the methods and reagents described by Hermanson 1996 (Ref. 26) Part II, Bioconjugate Reagents p. 169.

Examples of amino acids carrying a reactive functionality are the N-terminal amino acid with a free amino group, which can react with iodoacetic acid, and to which a protein can be linked, and amino acids that include two or more amino groups, two or more carboxyl groups, sulfhydryl groups, hydroxyl groups, halogen groups, aldehyde groups, alkenes, alkynes, thiocyanates, isothiocyanates, and ethoxide groups. The polypeptide according to this invention can include two or more different monomer unit amino acids with reactive functionalities, such as lysine and cysteine, and can include two or more different spacer monomer unit amino acids, such as alanine, glycine, proline, tryptophan, and homocysteic acid.

While participating in the iterative synthesis of the polymer of the invention, the functional groups in the functionalized monomer units can be protected with a suitable protective group that is subsequently removed. Suitable protective groups include benzyl, benzyloxycarbonyl, and ring substitution products thereof; t-butyl and t-butoxycarbonyl; 9-fluorenylmethoxycarbonyl, o-nitrophenylsulfonyl, 3-nitro-2-pyridinesulfenyl and dithiasuccinoyl. While so protected, the functional groups in the functionalized monomer units are preserved from reacting with reagents affecting other groups in the molecule; when it is desired that these functional group react, the groups are deprotected by reaction with an appropriate agent under the mildest possible conditions. Suitable deprotecting methods conditions include heating, catalytic hydrogenation, hydrolysis assisted by acid or base, and thiolysis or reductive exchange of a disulfide protecting group with a reagent containing a sulfhydryl group.

It is well known that the inclusion of even a single unit of certain amino acids can terminate an alpha helix or beta pleated sheet. This occurs because the introduction of one of these amino acids can result in a drastically different molecular geometry and consequent relative orientations of neighboring monomer units. Amino acids capable of changing the secondary structures of peptides include but are not limited to: one or more D-alpha-aminocarboxylic acid or proline monomer units. Where this effect is desired, for example in order to provide a more favorable orientation of the two members of a light emitting/light absorbing energy transfer pair, D-alanine and/or proline can be included in the polymer as spacer monomer units. A simple change in the number of amino acids between two tagged amino acids can significantly change their relative position (L. Pauling, 1960 (Ref. 28) p. 498).

Selective Cleavage

Selective cleavage of the polymer from the solid support can be carried out by a variety of methods: photolysis; catalytic hydrogenation; reaction with strong acids such as tri fluoroacetic acid, trifluoromethanesulfonic acid, hydrogen fluoride, and hydrogen bromide, preferably in the presence of a carbonium ion scavenger such as anisole or dimethyl sulfide; hydrolysis and alcoholysis catalyzed by nucleophiles such as ammonia, hydrazine, piperidine with dimethylformamide, tributylphosphine with sodium fluoride; reductive cleavage of disulfide bonds; and enzymes. The choice of selective cleavage agent, besides depending on the amino acid composition of the peptide, must be compatible with the chemistry of the other groups, moieties, and/or molecules bound by covalent bonds to the peptide.

In a preferred embodiment in which a lanthanide macrocycle and a protein, such as an antibody are linked to the polymer of the invention, both the lability of the macrocycle and the potential denaturation of the protein limit the choice of cleavage reagents. Strong chemicals, such as acids, bases, or any reaction involving organic solvents could cause either decomposition of the macrocycle or denaturation of the protein.

Two approaches to the cleavage of such peptide from the solid support are useful. One approach consists of attaching the peptide to the support via a disulfide linkage which can be cleaved by a reducing agent or by exchange with a sulfhydryl containing species, such as cysteine and its derivatives (Ref. 26). A limitation to the use of this approach is the fact that the agents suitable for the cleavage reduction often also reduce disulfide bonds that either serve to attach an analyte-binding species to the polymer, or are essential to the structural integrity of proteins, such as antibodies, that constitute an analyte-binding species.

The second and preferred approach consists of including into the polymer an amino acid sequence that can be specifically cleaved by an enzyme at a rate significantly faster than the rate of destruction of the protein that constitutes the analyte-binding species. As will be described, Proteinase K, when combined with the appropriate amino acid sequence, is sufficiently selective to permit the safe recovery of polymers still attached to an antibody capable of binding to its antigen. If a protein other than this specific antibody is used, then an enzyme that has minimal effect on the protein and has a readily hydrolyzable peptide substrate is used. If the monomers are nucleotides, the substrate can be a sequence specific for a restriction endonuclease, such as the rare-cutters, from Bacillus stearothermophilis and NotI from Nordcadia otitidis-caviarum (Strachan and A. P. Read, 1999) (Ref. 29). An extensive description of synthetic nucleic acid chemistry and means to tag nucleotides is found in (Ref. 26) Part III, 17. Nucleic acids pp 640-671, which is incorporated herein by reference.

Tags

Three types of tags are described in this invention: optical-labels, other-labels, and separation-tags.

Optical-Labels

Three types of optical-labels are described in this invention: luminescence-labels, fluorescence-labels, and absorbance-labels. It is highly desirable that species to be used as multiple luminescence-labels or fluorescence-labels should not suffer from concentration quenching. The best known examples of luminescence-labels that do not concentration quench are complexes containing lanthanide elements and having emission spectra with maxima in the range from 500 to 950 nanometers, such complexes consist of a trivalent lanthanide ion and an organic moiety.

Lanthanide-Containing Luminescence Labels

Particularly suitable luminescence-labels are the lanthanide-containing macrocycles, disclosed by L. Vallarino and R. Leif in U.S. Pat. No. 5,696,240, whose entire disclosure is incorporated herein by reference. The luminescence of the europium and samarium macrocycles can be enhanced by the addition of a solution which includes a nonluminescent trivalent lanthanide ion (Ref. 21).

Multiple M-Mac units linked to a polymer have the advantage of being insensitive to the concentration quenching that occurs with conventional organic fluorophores. Therefore, significant signal increase can be achieved by attaching a multiple M-Mac containing polymer to an analyte-binding species.

The complexes of europium(III), dysprosium(III), samarium(III) and terbium(III). while not significantly luminescent in themselves, possess a long-lived luminescence in the presence of an enhancer species. The enhancer species can be betadiketone molecules in solution, and can also be betadiketone groups present in the respective, europium, samarium, dysprosium, or terbium-tagged, polymers. In solution, these betadiketone molecules or betadiketonate groups are in equilibrium with the respective deprotonated species, namely the respective betadiketonate anions or betadiketonate groups. The intensity of europium(III) and/or samarium(III) luminescence with a common enhancer species can be further increased by interaction with a cofluorescence solution. The samarium(III) macrocycle (SmMac) has been found to simultaneously luminesce with the europium(III) macrocycle (EuMac) when a gadolinium(III)- or yttrium(III)-containing cofluorescence solution essentially identical to the one previously described and containing 1,1,1-trifluoro-4(2-thienyl)-1,3-butanedione (HTTFA), (Ref. 21) is employed. It was also found that the aliphatic diketone, 1,1,1-trifluoro-5,5-dimethyl-2-4-hexanedione (pivaloyltrifluoroacetone, HPTFA) interacts with both the terbium(III) macrocycle (TbMac) and the dysprosium(III) macrocycle (DyMac) to produce luminescent species. Therefore, it should now be possible to simultaneously and effectively employ four luminescent polymers, one labeled with a EuMac and emitting strongly in the red (ca. 618 nm), the second labeled with a SmMac and emitting in the orange and red at 564, 599, 645 and 652 nm, with the strongest SmMac emission occurring at 599 and 645-652 nm, the third labeled with a TbMac and emitting in the green (ca 545 nm), and the fourth labeled with DyMac and emitting in the blue and green at 480 and 575 nm.

It is also possible to increase the number of available optical-labels by employing species containing the same set of fluorophores in different relative amounts, with each mixed-fluorophore species serving as label for a given analyte, J. R. Kettman et al. 1998 (Ref. 30). A similar application is possible for the lanthanide macrocycles. Thus the narrow band emissions of lanthanides make them excellent choices for use by themselves, or in combination with one another, or in combination with other luminescent or fluorescent optical-labels.

According to this invention, the luminescent polymers tagged with Eu(III), Sm(III), Tb(III) and Dy(III) macrocycles can each be coupled to a different molecular species, which in turn is a member of a combining pair. In order to maximize the luminescence of each emitter—the Eu(III), Sm(III), Tb(III) and Dy(III) macrocycles—each emitter must interact with its optimal enhancing species. To this end, the solution containing the analytes to be detected/quantitated can be made up to include a common optimal enhancer for the EuMac and SmMac, for example HTTFA, and a separate optimal enhancer for the TbMac and DyMac, for example HPTFA. In such a situation, the luminescence of each of the lanthanides would be unavoidably decreased from its optimum level. Since the luminescence increasing ability of an enhancer depends on its electronic energy levels and is not related to a higher chemical affinity for the lanthanide it enhances, the probability that the EuMac, SmMac, TbMac, and DyMac would each have their two enhancer-binding positions occupied both by the appropriate enhancer would be reduced to about 25 percent in the presence of two "free" different enhancers in the common solution. It is also possible that an enhancer that is optimal for a first lanthanide ion would accept energy from the enhancer for a second lanthanide ion resulting in a significant diminution of the emission from the second lanthanide ion.

Another approach to achieving optimized luminescence for the EuMac, SmMac, TbMac and DyMac is to bind at least one of the enhancers to the same polymer that includes the lanthanide(III) macrocycle, in such a way that the geometric relationship between enhancer and lanthanide(III) macrocycle permits efficient energy transfer between the two species. For instance, multiple units of the betadiketone HPTFA, the anion of which (PTFA) preferentially enhances the luminescence of the TbMac and DyMac, can be bound to a polymer that contains multiple TbMac tags or multiple DyMac tags, whereas multiple units of the diketone HTTFA, the anion of which (TTFA) preferentially enhances the luminescence of the EuMac and SmMac, could be bound to a polymer that contains multiple EuMac tags or SmMac tags; both diketones being at all times in equilibrium with their respective anions. A peptide with a lanthanide-containing macrocycle and an enhancer attached to a neighboring amino acid monomer unit is represented by the schematic Formula VI:

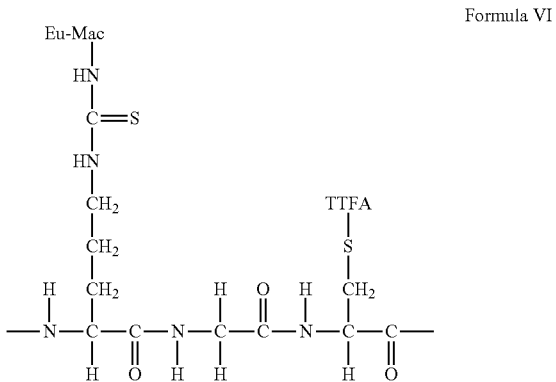

Formula VI

Formula VI is a schematic drawing of a peptide with a cationic Eu(III)-macrocyclic moiety (EuMac) bound by a thiourea linkage to a lysine and an anionic TTFA enhancer bound to the sulfur atom of a cysteine. in Formula VI, the relative position of the EuMac and the TTFA enhancer can be varied as required. Similar possibilities exist for PNAs and other lanthanide complexes. The presence of these polymer-bound enhancers also serves to stabilize the lanthanide macrocycle complex by providing a suitably located counterion-ligand that is attached to the same polymer chain.

Fluorescence-Labels

Fluorescence-labels are most commonly large organic molecules with double-bonded structures can be used singly or in combination to provide emission signals at different wavelengths. These fluorescence-labels usually have small Stokes shifts and their excitation and emission spectra partly overlap, resulting in the well-known phenomenon of fluorescence quenching when the individual absorbers/emitters are closely spaced on a polymer or other carrier. This effect, which is due to the transfer of energy between adjacent absorbers/emitters, can be minimized by designing and synthesizing, peptides in which the fluorescence-labels are spaced sufficiently apart, preferably by a distance greater than 50 Angstroms. There is a trade-off between the theoretical energy transfer efficiency, which is inversely proportional to the sixth power of the distance between the energy accepting and emitting species, Stryer and Haugland, 1967 (Ref. 31), and maximizing the number of fluorescent optical-labels that can be attached to a peptide. However, it has been reported that this inverse sixth power relationship is not always observed, Y. Li and A. N. Glazer, 1999 (Ref. 32). Thus, the optimum spacing between labels must be determined by experiment.

The preceding considerations also apply to appropriate combinations of organic fluorophores that can be specifically and sequentially linked to a peptide or other polymer according to the invention. With polymers containing multiple pairs of appropriately spaced different fluorophores, it becomes possible for a single light source, such as an Argon ion laser with a 488 nm output, a mercury arc with a 365 nm output, or a HeNe or semiconductor laser, to excite two or more fluorophores with well separated excitation and emission spectra, but so selected that the emission spectrum of the "shorter-wavelength" excited fluorophore overlaps the excitation spectrum of the "longer wave-length" excited fluorophore. When the "shorter-wavelength" member of such an energy-transfer pair absorbs radiant energy and is excited, it transfers its energy through a nonradiative process to the "longer-wavelength" member, which is then excited and emits energy at its own characteristic wave-length. The close proximity of these energy-donor energy-transfer pairs maximizes the efficiency of energy transfer. Conversely, the separation of like fluorophores minimizes radiationless losses.

Effective energy transfer between two or three appropriately positioned fluorophores can result in an increased separation between excitation and emission wavelengths, providing sets of fluorescent-labels that absorb at the same wavelength but emit at different wavelengths. For example, the following situation can exist: one label contains fluorophore A and produces A's typical emission. A second label contains fluorophores A and B; in this second label, A absorbs light at its usual wavelength and transfers energy to B, which then emits light at considerably longer wavelength than A itself. A third label contains fluorophores A, B and C, such that A absorbs light at its usual wavelength and transfers energy to B, which in turn transfers energy to C, and C finally emits light at longer wavelength than either A or B. Since the sequential synthesis of polymers from monomers with different side-chain reactive functionalities permits the manufacture of species with an effective spatial organization of light emitting and absorbing species, such sequential synthesis greatly improves the availability of fluorophore combinations capable of this energy absorbing/energy emitting cascade effect. The members of each energy-transfer set can be linked to monomer units located at specific positions along the polymer, in such a way that the distance between the members of each set, as well as their relative geometric orientations, provide efficient energy transfer between donor(s) and acceptor(s) and minimize concentration quenching. Suitable energy transfer combinations include alpha-napthyl groups and dansyl groups in the same molecule (Stryer and Haugland 1967), (Ref. 31); fluorescein and tetramethylrhodamine, 6-carboxylluorescein and 5-carboxy-X-rhodamine (Li and Glazer 1999), (Ref. 32); R-phyeoerythrin (PE) and the cyanine dye Cy5™ (Waggoner, et al. 1993), (Ref. 33); phycoerythrin-texas red (Ref. 34), phycoerythrin-cyanin 5.1 (Ref. 34); and Peridinin-chlorophyll (Recktenwald, U.S. Pat. No. 4,876,190, 1989), (Ref 35).

By taking advantage of the well-known secondary structures of peptides, such as alpha helices and beta pleated sheets, the distance and geometry between fluorescence-labeled monomers in peptides according to the invention can be computed and multiple polymers according to the invention can be synthesized with the technology of combinatorial chemistry; their fluorescence and/or luminescence spectra can serve as a screen to determine potential candidates for optical-labels in tagged-peptides created and used according to the teachings of this patent.

Absorbance-Labels

Tagged-polymer-analyte-binding species containing multiple absorbance-labels can be used in fields such as light microscopy and other analytical techniques, such as gel electrophoresis. These tagged-polymer-analyte-binding species can replace the use of light absorbing enzyme products or light absorbing species produced by reactions involving enzyme products, and offer the advantage of employing a single antibody binding procedure, eliminating the need for pretreating the sample to reduce background and of following the binding of the antibody by an enzymatic development step. Tagged-polymer-analyte-binding species can eliminate the background absorbance associated with enzymatic reactions and provide selectivity of the light absorbing species with appropriate maxima, maximal extinction, and minimal spectral width. High absorbance intensity can be achieved by linking, according to this invention, multiple chromophores to monomer units in a polymer. These chromophores can be conventional absorbance dyes or fluorescent species with a high molar absorbance, because fluorescence quenching has no significant effect on the increased absorbance provided by multiple light-absorbing moieties. An extensive description of light absorbing dyes of which many could serve as the basis of absorbance-labels is found in Gurr, 1971 (Ref. 36), which is incorporated herein by reference.

Other-Labels

Two types of other-labels are described in this invention: radioactive-labels and paramagnetic-labels. Radioactive-labels consist of any radioactive element or any element that can be induced to become radioactive and can be part of, or bound to, a monomer unit in the polymer of this invention. A particularly suitable radioactive-label is $^{90}$Y chelated to 1,4,7,10-tetraazacyclododecane-N,N',N'',N'''-tetraacetic acid, DOTA; J. J. Peterson and C. F. Meares 1999 (Ref. 10). This radioactive-label can be formed by neutron bombardment from the nonradioactive Yttrium(III) macrocycle-monoisothiocyanate containing the isotope $^{89}$Y.

Paramagnetic-Labels

Paramagnetic-labels are species containing metal ions that have partly unfilled electron shells and hence possess permanent magnetic moments; certain paramagnetic labels can serve as contrast agents for magnetic resonance imaging (MRI). A paramagnetic label particularly suitable for this use is the gadolinium(III) macrocycle-mono-isothiocyanate. Polymers containing multiple gadolinium(III) complexes, which have high isotropic magnetic moments, can provide increased relaxivity for contrast enhancement in clinical magnetic resonance imaging. Attachment of a polymer carrying multiple gadolinium ions to a suitable biomolecule further permits the targeting of the contrast agent to selected organs. The ordered synthesis of the polymers permits maximizing the localized gadolinium content while minimizing the general toxicity.

Separation-Tags

Four types of separation-tags are described in this invention: paramagnetic, charged, mass increasing, and density changing species; all these separation-tags increase a specific physical property of the species to which they are bound. Thus, a molecule, particle, or cell bound to a polymer-analyte-binding species that is tagged with separation-labels will move under the appropriate force.

Paramagnetic separation-tags are species that contain highly paramagnetic metal ions. A molecule, particle, or cell attached to a polymer-analyte-binding Species tagged with multiple paramagnetic separation-tags will migrate under a magnetic field gradient. Particularly useful for this purpose are the erbium(III) and holmium(III) macrocycle-mono-isothiocyanates.

Charged-tags are species that contain highly charged metal ions. A molecule, particle or cell will change its net electrical charge after being attached to a polymer-analyte-binding species where the polymer includes multiple charged-tags. This will change both the electrophoretic mobility and the isoelectric point oldie molecule, particle or cell. Electrophoresis is a standard technique for separating molecules, particles, or cells under the effect of an electrical field. Each lanthanide (III) macrocycle adds a net charge of +3 to the polymer of a tagged-polymer-analyte-binding species and the bound molecule, particle, or cell.

Mass increasing tags and density changing tags are species that contain heavy metal ions; these tags increase the mass and the mass per unit volume, respectively, of any species to which they are attached. The increase in mass resulting from a mass-tag increases the response of the molecule, particle, or cell bound to a tagged-polymer-analyte-binding species to the application of a gravitational field, such as that induced by centrifugation. Similarly, a density-tag provides an increase in density. Gravitational fields are used to separate molecules, particles, and cells by both sedimentation velocity and buoyant density. Particularly useful for this purpose are the erbium(III) and holmium(III) macrocycle-mono-isothiocyanates.

Analyte-Binding Species:

There is also provided, according to this invention, a tagged-polymer-analyte-binding species comprising an analyte-binding species covalently attached to a tagged-polymer. Preparation of this tagged-polymer-analyte-binding species is facilitated if the analyte-binding species reacts with the tagged-polymer while the latter is still attached to the solid support. This tagged-polymer-analyte-binding species can be represented by Formula VII, which shows the analyte-binding species, symbolized by ABS, linked to the polymer of the invention represented by Formula III above:

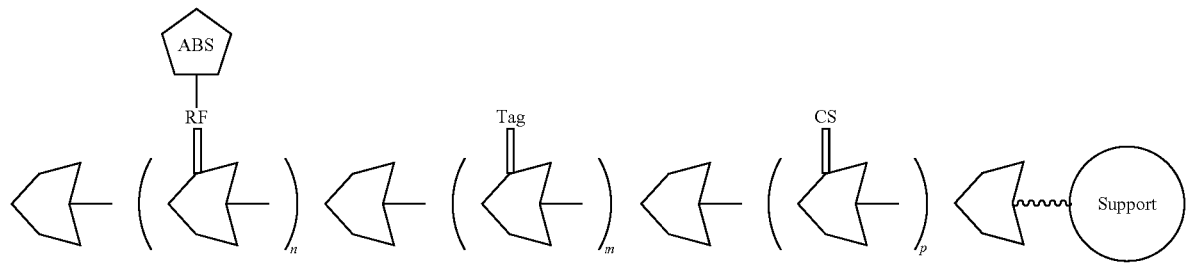

Formula VII

As in Formula III, each left pointing broad-arrow shape represents a monomer unit; RF represents a reactive functionality linked to a monomer unit; Tag independently at each occurrence represents an optical-label, other-label, or separation-tag linked to a monomer unit; CS represents a cleavable link to the solid support shown by the circular shape at the right; the pentagon labeled ABS represents an analyte-binding species, linked by a covalent bond to a reactive functionality of the monomer and thus attached to the polymer. Broad-arrow shapes without other indication represent spacer monomer units: n, m, and p are numbers defined as above.

For certain uses, the tagged-polymer-analyte-binding species is freed from the support by selectively cleaving the cleavable link. The freed tagged-polymer-analyte-binding species can be represented by Formula VIII:

Formula VIII

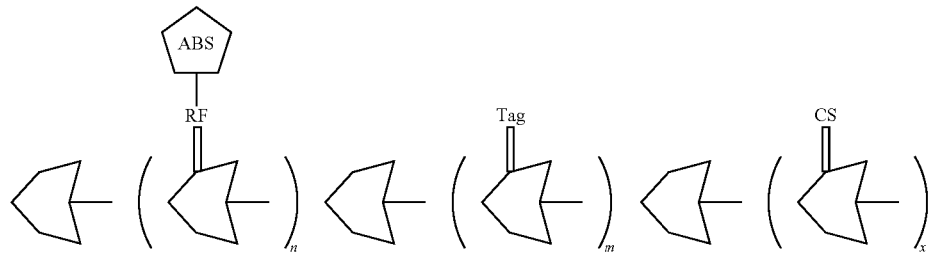

in which, as in Formula VII, each left pointing broad-arrow shape represents a monomer unit; RF represents a reactive functionality linked to a monomer unit; Tag independently at each occurrence represents an optical-label, other-label, or separation-tag, linked to a monomer unit; CS represents the monomer unit that was part of the cleavable link to the support; x is a number from 1 to 25 and is less than or equal to p of Formula VII; the pentagon labeled ABS represents an analyte-binding species, which has formed a covalent bond with a reactive functionality and thus is attached to the polymer; broad-arrow shapes without other indication represent spacer monomer units; and the numbers n and m are as defined above.

The number of spacer monomer units such as spacer amino acids in a polypeptide according to the invention is governed by a balance of the cost of synthesis and the optimal number of spacers required to provide the desired three-dimensional conformation of the peptide. It can reasonably range from 0 to (20×m)+100. Spacer monomers can be intercalated as appropriate within or between groups of both tag-bearing and reactive functionality-bearing monomers. From 1 to 10 types of tags can be linked to monomer units.

When the polymer according to the invention is a peptide, the left pointing broad-arrow shapes with posts attached represent amino acids to which a tag or a reactive functionality can be linked, and the broad-arrow shapes without posts represent spacer amino acids. Non-limiting analyte-binding species include: proteins including antibodies; avidin and its derivatives and variants; streptavidin; nucleic acids and their analogs including DNA, RNA, and peptide nucleic acids (PNAs); lectins and analytes which are the tagged species in competitive assays. Many of the molecular genetic techniques required for the development and use of nucleic acid analyte-binding species are described in T. Strachan and A. P. Read, Human Molecular Genetics 2nd ed 1999 (Ref. 29).

Before or subsequent to coupling to a protein, antibody, nucleic acid, other member of a specific combining pair, or extension to include a PNA, the polymer according to the invention, such as a polypeptide, can be combined with any of the aforementioned species capable of forming a covalent bond with the reactive functionality of a monomer unit, such as a functionalized amino acid. For instance, lysine residues can react with the EuMac-mono-NCS. Cysteine residues, or other thiol-containing amino acids, can react with other thiols or with iodinated species of functionalized enhancers, March, 1985 (Ref. 37). Conversely, incorporation of an aliphatic iodine-bearing group in an amino acid can provide reactivity with thiols and other species. The result of each of the above-mentioned approaches will be a peptide containing luminescent or related molecules covalently bound in a specific order to some of its side chains. This peptide can be extended to form a PNA, or it can be terminated with a species which includes a reactive functionality capable of linking to a protein, nucleic acid, haptene or other relevant species employed in clinical assays. Both charged and uncharged naturally occurring or synthetic amino acids can be incorporated in the peptide for the purposes of increasing water solubility and minimizing nonspecific binding.

If the tagged-polymer, according to the invention, terminates in an oligonucleotide, this first oligonucleotide can be terminated by a sequence which is complementary to a region of a second oligo-nucleotide or polynucleotide. The two complementary regions of the first oligonucleotide and the second oligonucleotide or polynucleotide can hybridize. The first oligonucleotide can then be enzymatically extended in the presence of the 4 nucleotide triphosphates to form a region complementary to the second oligonucleotide or polynucleotide. This product after denaturation and separation from the second oligonucleotide or polynucleotide will be tagged-analyte-binding species that can be used to detect the sequences present in the second oligonucleotide or polynucleotide.

Procedure

There is also provided, in accordance with this invention, a process for preparing a tagged water-soluble polymer comprising a plurality of tagged monomer units and spacer monomer units, with at least one of the tagged monomer units being tagged with an optical-label, or other-label, or separation-tag. The process consists of the following steps:

a) Providing a first monomer having 2-3 reactive functionalities, of which one is free and the remainder are protected, b) reacting the free reactive functionality of the first monomer with a water-insoluble support so as to link the monomer to the support, c) deprotecting one protected reactive functionality of the monomer, d) providing a second monomer having 2-3 reactive functionalities, of which one is free and the remainder are protected; the first monomer and the second monomer can be the same or different, e) reacting the second monomer with the product of step c), thereby linking the second monomer to the support through the first monomer, f) deprotecting one remaining protected reactive functionality of the second monomer, g) repeating steps d), e), and f) with additional monomers having 2-3 reactive functionalities of which one is free and the remainder are protected, the additional monomers being the same as, or different from, the first and/or second monomer, thereby linking the additional monomers in predetermined number and sequence to the support through the first monomer and the second monomer, to yield a polymer comprising units of monomers in the number and sequence in which they have been reacted and linked to the support, h) as appropriate, sequentially or simultaneously deprotecting some or all of the protected reactive functionalities,
i) as appropriate, sequentially or simultaneously reacting one or more tag(s), each with a specific type of polymer-bound reactive functionality, to produce a tagged-polymer
j) coupling an analyte-binding species to a specific type of polymer-bound reactive functionality to produce a tagged-polymer-analyte-binding species
k) selectively cleaving the tagged-polymer-analyte-binding species from the support.

This sequence of steps produces a polymer that contains: at least one monomer unit linked to a tag including an optical-label capable of absorbing and/or emitting light at a wavelength between 200 and 1,400 nanometers, an other-label that is paramagnetic, or radioactive, or a separation tag that is a paramagnetic, or charged, or mass increasing, or density changing species; at least one monomer unit bearing a reactive functionality; and at least one spacer monomer unit. The molecular weight of the polymer of this invention is at least that of the essential three monomer units defined above. There is in principle no upper limit except the practical consideration that the added cost of more monomer units be justified by added benefits of their presence. Hence the polymer of the invention preferably includes from 3 to 1000 monomer units and more preferably has a molecular weight in the range from 1000 to 100000 daltons.

In this process of the invention, the tag can be an optical-label consisting of a macrocyclic complex of a lanthanide(III) ion. Particularly suitable are macrocyclic complexes in which the lanthanide ion is europium(III), samarium(III), dysprosium(III), or terbium(III).

The selective cleavage of the polymer from the support can be carried out by such mild techniques as enzymatic hydrolysis or disulfide reduction. In special cases, where both the tag and the analyte-binding species are both sufficiently resistant, cleavage can be achieved by photolysis, catalytic hydrogenation, or hydrolysis in presence of a nucleophilic catalyst or of a strong acid such as hydrofluoric acid or trifluoromethanesulfonic acid.

When the monomers provided to the process are alpha-aminocarboxylic acids, the resulting polymer is a tagged polypeptide bearing a reactive functionality for linking to an analyte-binding species.

Also in accordance with this invention, there is provided a method for the manufacture of the tagged-analyte-binding species. This method includes the steps of:
1. Producing a polymer that is bound to a solid support and contains three types of sites of known composition and sequence, as well as spacer monomer units. The first type of site includes either a sequence of monomers that can be specifically cleaved to permit the separation of the polymer from the solid support, or a single monomer that is coupled to the support by a bond that can be specifically cleaved. The second type of site includes either reactive functionalities or functionalities that include, are, or can be covalently coupled to, such tags as optical-labels, other-labels, or separation-tags. The third type of site has a specific reactive functionality capable of forming a covalent bond with an analyte-binding species. Additionally, the polymer can include spacer monomer units within and/or between these sites. The polymer contains at least one of each type of site and can contain more than one of each type, up to a practical upper limit where the added benefit of an additional site no longer justifies the effort of the added synthetic steps.
2. Deprotecting, if needed, specific reactive functionalities of monomer units in order to permit the coupling of tags to the monomer units by reaction with the deprotected reactive functionalities, if the tagged monomers are not already present because they were directly incorporated in the polymer.
3. Forming a specific covalent bond between a monomer unit with a reactive functionality and an analyte-binding species, such that number of monomer units so bonded equals the number of molecules of the analyte-binding species and is from 1 to 10 for each site of known composition and sequence.

Such a polymer can be represented by the schematic Formula IX:

Formula IX

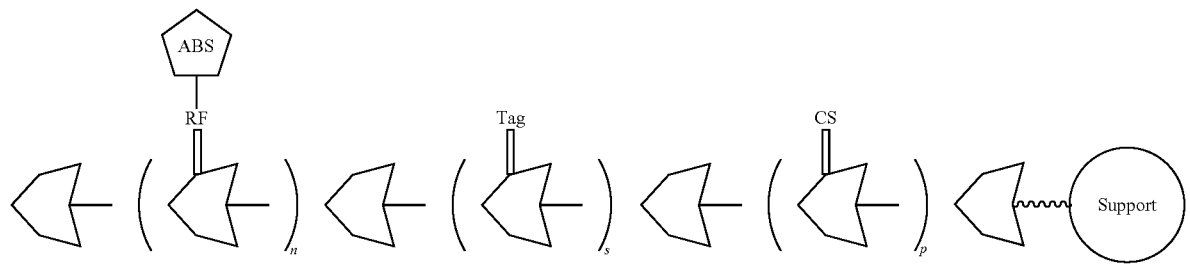

wherein each left pointing broad-arrow shape represents a monomer unit; RF represents a reactive functionality linked to a monomer unit; Tag independently at each occurrence represents an opticallabel, other-label, or separation-tag linked to a monomer unit; CS represents a cleavable link to the solid support shown by the circular shape at the right; the pentagon labeled ABS represents an analyte-binding species linked to the polymer by a covalent bond to a monomer unit through a reactive functionality; broad-arrow shapes without other indication represent spacer monomer units, n is a number from 1 to 10, s is a number from 2 to 1000, and p is a number from 1 to 25.
4. Specifically cleaving the tagged-analyte-binding species from the solid support and releasing it into solution.
5. Such a polymer can be represented by the schematic Formula X:

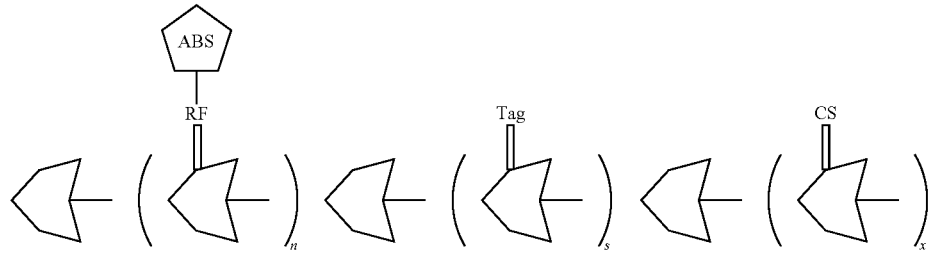

Formula X wherein, each left pointing broad-arrow shape represents a monomer unit: RF represents a reactive functionality linked to a monomer unit; Tag independently at each occurrence represents an optical-label, other-label, or separation-tag linked to a monomer unit; the pentagon labeled ABS represents an analyte-binding species linked to the polymer by a covalent bond to a monomer unit through a reactive functionality; broad-arrow shapes without other indication represent spacer monomer units, n is a number from 1 to 10, s is a number from 2 to 1000, and x is a number from 1 to 25 and is less than or equal to p of Formula IX.

The product of Step 2 can be stored as well as shipped. Hence, Steps 3 and 4 can be performed at any time after step 2, and the equipment and expertise required for steps 3 and 4 are much less than those required for steps 1 and 2. Accordingly, it is possible for a user to perform these later steps conveniently at his/her own place of work, so that users dealing with many varieties of analyte-binding species will be able to label them and ship them on demand.

The methodology of the present invention affords advantages compared to that of Peterson and Meares, 1998 (Ref 9) because the purpose of the enzymatic cleavage of the peptide from the support is to manufacture a tagged-analyte-binding species used to produce an in vitro reagent. The reagent of this invention no longer includes the complete enzyme (Proteinase K) cleavable site. Peterson and Meares, 1999 only used the enzymatic cleavage (cathepsin B or cathepsin D) on the bead-bound peptides as a means to select sequences that would be cleaved in vivo. No enzymatic step was included in their preparation.

The methodology of the present invention offers advantages compared to that of Takalo et al. (Ref. 11) because: 1) the multiple fluorescing or luminescing containing moieties are coupled to a carrier; rather than being directly coupled to a biological molecule. The present invention permits a large number of fluorescing or luminescing moieties to be attached with minimal loss of biological activity. 2) The chemical reactions employed for the attachment of the fluorescent or luminescent moieties are not limited to conditions that permit the retention of biological activity or the retention of the chemical integrity of the biomolecule.

The methodology of the present invention affords advantages compared to that of Kwiatkowski et al. (Ref. 13) because the luminescent or fluorescent species that constitute the optical-labels in the preferred embodiment are added after the peptide or polymer carrier has been synthesized on the solid support, and thus they are not subjected to the conditions required for any of the chemical reactions involved in the synthesis of the polymer.

The methodology of the present invention affords advantages compared to those of both Takalo et al. (Ref. 11) and Kwiatkowski et al. (Ref. 13) because: 1) The tagged-polymer can be pre-manufactured and stored for subsequent use. 2) A biological analyte can be coupled to the tagged-polymer, containing luminescent or fluorescent optical-labels, under mild and/or physiological condition with minimal loss of biological activity. 3) The luminescent or fluorescent tagged biomolecule can be prepared for use with minimal equipment. and 4) The relative positions of fluorescent or luminescent labeled groups can be controlled by the choice of their binding monomer, position, and intermediate spacer monomers. The well known ability of peptides to form secondary and tertiary structures can be employed to control the position and orientations of fluorescent and/or luminescent species.

The methodology of the present invention affords advantages compared to that of Salo et al. 1998 (Ref 14) because 1) The tagged-polymer can be pre-manufactured and stored for subsequent use. 2) An oligonucleotide can be attached without the use of specialized, expensive instrumentation. 3) Enzymes can be used for selective cleavage of the polymer of the invention from the support. 4) A controlled geometry of the tagged monomer units can minimize radiationless losses between fluorescent species and between luminescent species with broad emissions. 5) A controlled geometry of the tagged monomer units can permit energy transfer between optical labels and 6) the polymer can be a peptide or PNA or any other species capable of sequential synthesis.

Since multiple-optical-label polymers according to the invention provide greater signals than single optical-labels, they can be useful particularly as reporter molecules in immunoassays, analytical cytology, histological staining, and imaging processing. Multiple-optical-label polymers where the tag is a lanthanide macrocycle disclosed in U.S. Pat. No. 5,373,093 have the further advantages that the large Stokes shift, narrow band-width of the emission, enhancement of the emission by cofluorescence, and time gated luminescence minimize the background noise. Thus, the signal can be maximized simultaneously with the noise being minimized. These luminescent polymers can be attached by a coupling functionality to small molecules, such as nucleic acid bases or haptens, or to large molecules like proteins, antibodies, or nucleic acids. These luminescent polymers can be linked to polynucleotides, peptide nucleic acids (PNAs), peptides, or polysaccharides.

Tags consisting of optical-labels, especially fluorophores, often require the presence of certain proximal molecules or groups for efficient energy transfer and other purposes. The use of polymer carriers according to the invention permits different molecular species to be structured in three-dimensional space to maximize the energy transfer from one optical-label to another. Luminescence enhancer species which absorb light and transfer energy to the lanthanide can be located within the polymer structure in such a way that they can either complex directly with the lanthanide(III) ion of macrocyclic complexes, or transfer energy to an enhancer which is already directly complexed with the lanthanide(III)

macrocycles. Thus, the sequential synthesis, according to the invention, of polymers from monomers with different sidechains permits the manufacture of species with an effective spatial organization of light emitting and light absorbing species.

It is a feature of this invention that the polymers with functionalized side chains provide a means for attaching multiple luminescent lanthanide macrocycles to a single member of a combining pair or analyte-binding species resulting in increased signal; whereas the coupling to a polymer of multiple units of a conventional organic fluorophore, such as fluorescein, has not resulted in a significant increase in fluorescence compared to a single fluorophore unit. Therefore, the proportionality between luminescence intensity and macrocycle loading of a polymer, which is an essential aspect of the present disclosure, is not consistent with previous observations and hence is novel and unexpected.

Three ways to covalently bind species with special desired properties (e.g. luminescence) to a peptide backbone are: 1) Synthesize amino acids which have appropriately functionalized and protected side chains and directly incorporate the species in the appropriate order as the peptide is synthesized. 2) Sequentially react a growing peptide, after the addition of a functionalized amino acid, with a species capable of forming a bond with the reactive functionality of said amino acid. The growing peptide presumably would be bound to a solid substrate. The species could be: an organic molecule (optical-label, luminescence enhancer, etc.), a metal ion containing macrocycle, or a chelate. 3) Include in the same peptide multiple amino acids with different reactive functionalities.

The luminescent polymers of the preferred embodiment of this invention are unique in several significant respects. The combination of properties which sets them apart from other fluorophores or fluorophore-binding polymers includes one or more of the following: a monotonic relationship between the number of luminescent species incorporated and luminescence intensity, reproducible organized location of two or more molecular species capable of energy transfer from one species to another without direct covalent bonds between the species, solubility in aqueous solutions, controlled ionic charge and controlled hydrophobicity-hydrophilicity to minimize nonspecific binding, and large Stokes shifts resulting from separation between excitation and emission spectra.

Analytes linked to an analyte-binding, species are conveniently grouped by molecular weights. One group of such analytes consists of compounds that have molecular weights in the range of about 125-2,000 daltons and include a wide variety of substances, which are often referred to as haptens. These compounds include:
a) Vitamins, vitamin precursors, and vitamin metabolites including retinol, vitamin K, cobalamin, biotin, folate;
b) Hormones and related compounds including:
  (i) steroid hormones including estrogen, corticosterone, testosterone, ecdysone;
  (ii) amino acid derived hormones including thyroxine, epinephrine;
  (iii) prostaglandins;
  (iv) peptide hormones including oxytocin, somatostatin;
c) pharmaceuticals including aspirin, penicillin, hydrochlorothiazide;
d) Nucleic acid constituents including:
  (i) natural and synthetic nucleic acid bases including cytosine, thymine, adenine, guanine, uracil, derivatives of said bases including 5-bromouracil;
  (ii) natural and synthetic nucleosides and deoxynucleosides including 2-deoxyadenosine, 2-deoxycytidine, 2-deoxythymidine, 2-deoxyguanosine, 5-bromo-2-deoxyuridine, adenosine, cytidine, uridine, guanosine, 5-bromouridine;
  (iii) natural and synthetic nucleotides including the mono, di, and triphosphates of 2-deoxyadenosine, 2-deoxycytidine, 2-deoxythymidine, 2-deoxyguanosine, 5-bromo-2-deoxyuridine, adenosine, cytidine, uridine, guanosine, 5-bromouridine;
e) drugs of abuse including cocaine, tetrahydrocannabinol;
f) histological stains including fluorescein, DAPI;
g) pesticides including digitoxin;
h) and miscellaneous haptens including diphenylhydantoin, quinidine, RDX.

Another group of analytes consists of compounds having a molecular weight of 2,000 daltons or more; including:
a) proteins and their combinations including:
  (i) albumins, globulins, hemoglobin, staphylococcal protein A, alpha-fetoprotein, retinol-binding protein, avidin, streptavidin, C-reactive protein, collagen, keratin;
  (ii) immunoglobulins including IgG, IgM, IgA, IgE;
  (iii) hormones including lymphokines, follicle stimulating hormone, and thyroid stimulating hormone;
  (iv) enzymes including trypsin, pepsin, reverse transcriptases;
  (v) cell surface antigens on T- and B-lymphocytes, i.e. CD-4, CD-8, CD-20 proteins, and the leukocyte cell surface antigens, such as described in the presently employed CD nomenclature;
  (vi) blood group antigens including A, B and Rh;
  (vii) major histocompatibility antigens both of class 1 and class 2;
  (viii) hormone receptors including estrogen receptor, progesterone receptor, and glucocorticoid receptor;
  (ix) cell cycle associated proteins including protein kinases, cyclins, PCNA, and p53;
  (x) antigens associated with cancer diagnosis and therapy including BRCA(s), carcinoembryonic antigen, HPV 16, HPV 18, MDR, c-neu; tumor surpressor proteins, p53 and retinalblastoma;
  (xi) apoptosis related markers including annexin V, bak, bcl-2, las caspases, nuclear matrix protein, cytochrome c, nucleosome;
b) toxins including cholera toxin, diphtheria toxin, and botulinum toxin, snake venom toxins, tetrodotoxin, saxitoxin;
c) lectins including concanavalin, wheat germ agglutinin, soy bean agglutinin;
d) polysialic acids including chitin;
e) polynucleotides including:
  (i) RNAs including segments of the HIV genome, human hemoglobin A and F messenger RNAs;
  (ii) DNAs including chromosome specific sequences, centromeres, telomere specific sequences, single copy sequences from normal tissues, single copy sequences from tumors.

Summary of Equipment, Instruments, General Procedures and Materials Equipment, Instruments and General Procedures In reporting quantities and concentrations, the term "micro" will be conventionally abbreviated as µ; for example, microgram will be abbreviated as µg.

All glassware for Example I to Example III was cleaned with a methanol/concentrated hydrochloric acid mixture (90/10 v/v), rinsed with deionized water and methanol, and dried at 60° C.

All aqueous solution of Example I to Example III were prepared using deionized water (MILLIPORE, MILLIQ® Water, >18 MOhm resistance); CULLIGAN distilled water 5 gallon is and was used in Example IV onwards.

Atomic absorption analyses of europium, samarium and terbium were performed on a Varian SpectraAA instrument, using as reference the elemental standards from ALDRICH Chemical Co. (Eu, Catalog No. 20,712-8; Sm, 20,745-4; Tb, 30,592-8, 1996-97); selected samples were analyzed by ICP-AES (Schneider Laboratories, Richmond, Va.).

Fluorescence spectra of solutions were obtained with an SLM Model 8000 photon-counting spectrofluorimeter. Samples were examined in stoppered triangular quartz cuvettes, so oriented that the excitation beam entered the diagonal face at a 45 degree angle and the emitted light was collected through the bulk of the sample at 90 degrees relative to excitation.

Visible/ultraviolet absorption spectra of solutions in Example I to Example III were obtained with a Shimadzu UV-265 ultraviolet-visible recording spectrophotometer, using stoppered quartz cuvettes. In Example IV to Example VII spectra were obtained with a Shimadzu UV 2401 PC model # 206-82301-92 spectrophotometer; samples were examined in stoppered 40 microliter quartz cuvettes (Starna, 16.40-Q-10).

In experiments with peptide-bound PEGA beads (see next section), removal of supernatant was performed as follows: the PEGA beads with bound peptide were allowed to settle by gravity for approximately one minute prior to removing the supernatant fluid with a Gilson PIPETMAN® P200 and Fisher Brand 200 μL pipetting tips (FISHER SCIENTIFIC Catalog No. 21-197-2K). The fine bore of the pipetting tips prevented the entrance of the beads.

EPPENDORF® Safe-Lock 1.5 mL microcentrifuge tubes, Catalog Number 22 36 320-4 (EPPENDORF TUBES) were used in all operations with the PEGA beads with bound peptide.

All experiments and measurements were performed at ambient temperature unless stated otherwise.

All spectra were transferred to and graphed using a spreadsheet, Microsoft Excel.

Most Commonly Used Materials (a) Hexamethylenetetramine (HMTA), ACS Reagent, ALDRICH Chemical Co., Catalog No. 39,861-0 (1999).
(b) Tris(hydroxymethyl)aminomethane (TRIS), ACS Reagent, ALDRICH Chemical Co., Catalog No. 25, 285-9 (1996-97), (Example I to Example III). Examples IV onward, Ameresco Ultra Pure Grade, Catalog No. 0497-1 Kg.
(c) Dimethylsulfoxide (DMSO), ACS Reagent, spectrophotometric grade, ALDRICH Chemical Co., Catalog No. 15, 493-9 (1996-97), (Example I to Example III).
(d) EuMac-di-NCS, prepared according to procedures of Examples XI and XXX VI B. Step 1, of U.S. Pat. No. 5,696,240.
(e) 4,4,4-trifluoro-1(2-thienyl)-1,3-butanedione (thenoyltrifluoroacetone, HTTFA), ALDRICH Chemical Co., Catalog No. T2, 700-6 (1996-97). For Example I to Example III, commercial HTTFA was purified by recrystallization from ethanol(charcoal)/hexane and stored at 4° C. in a dark glass container. From Example VII onwards, the HTTFA was used as received.
(f) Aspartic acid, >99%. SIGMA® Catalog No. A8949 (1998)
(g) SEPHADEX™ G-25 Superfine, AMERSHAM PHARMACIA, Code No. 17-0031-01 (1998-99).
(h) High purity Gd(III) trichloride chloride hydrate (Example I to Example III), $GdCl_3.n(H_2O)$, prepared from the oxide, $Gd_2O_3$ 99.999% REO, ALPHA AESAR®, Catalog No. 11289 (1999-2000), by dissolving it in 15% aqueous HCl, followed by evaporation to dryness with mild heating under reduced pressure. From Example VII onwards, $GdCl_3.6H_2O$ 99.99%, ALFA AESAR®, Catalog No. 11287 (1999).
(i) 1,10-Phenanthroline (Phen), ALDRICH Chemical Co., Catalog No. 13, 137-7 (1999).
(j) Cetyltrimethylammonium bromide (CTAB), ALDRICH Chemical Co., Catalog No. 85,582-0 (1999).
(k) Trioctylphosphineoxide (TOPO), ALDRICH Chemical Co., Catalog No. 22,330-1 (1999).
(l) The cofluorescence solution was prepared according to J. R. Quagliano et al. 2000 (Ref. 21) (cofluorescence solution).
(m) The hydrophilic support for peptide synthesis and manipulation was PL-PEGA Resin (Polymer Laboratories), which is described by the vendor as Acryloylated bis(2-aminopropyl)poly-ethylene glycol/dimethyl acrylamide copolymer, nominal particle size 300-500 um, nominal loading 0.2 mMol/g, abbreviated as PEGA.
(n) Proteinase K Molecular Biology, 23 mg/mL protein, 1,100 units, solution in 40° A glycerol (v/v) containing 10 mM Tris-HCl, pH 7.5, with 1 mM calcium acetate, SIGMA® Catalog. No. P-4850 (2000).
(o) H-Cys(Npys)-Trp-Lys-Lys-Lys-Pro-Ala-Pro-Phe-Ala-Ala-Ala-LC-PEGA resin custom synthesis, ANASPEC, Peptide Name: NIRL-2.

Common inorganic acids, bases, and salts were obtained from ordinary commercial sources. Information for less commonly used materials will be provided in the Examples, as appropriate.

Example I

Synthesis of a Luminescent Lysine Homopolymer with Side Chains Consisting of a Hexa-Aza-Macrocyclic Complex of Europium(III)

A. Materials
(a) EuMac-di-NCS (3.78 mg, $4.0 \times 10^{-3}$ mol) dissolved in 0.900 mL of DMSO (EuMac-di-NCS DMSO solution).
(b) HMTA aqueous solution (0.267 M) adjusted to pH 9.4 with NaOH (0.267 M HMTA pH 9.4 buffer).
(c) Lysine homopolymer (5.1 mg, $5.5 \times 10^{-5}$ mol) SIGMA® Catalog No. P-1274, m.wt. 93,000 dissolved in a mixture consisting of 0.400 mL DMSO and 1.00 mL 0.267 M HMTA pH 9.4. buffer (polylysine HMTA solution).
(d) HTTFA ethanol solution ($5.00 \times 10^{-2}$ M in ethanol-water), (HTTFA solution). The solution was prepared by dissolving 1.100 g of solid HTTFA in 5.00 mL of ethanol and diluting the resulting solution to a total volume of 50.00 mL with deionized water. The solution was protected from light and stored in a refrigerator at 4° C.
(e) HMTA, 10% aqueous solution (0.267 M), adjusted to pH 7.6 with hydrochloric acid, (0.267M HMTA pH 7.5 buffer).
(f) HMTA aqueous solution (0.71 M) adjusted to pH 6.0 with HCl, (0.71 M HMTA pH 6 buffer).
(g) Aspartic acid aqueous solution ($2.0 \times 10^{-2}$ Ni), (aspartic acid solution).

B. Procedure
  (a) The EuMac-di-NCS DMSO solution (0.150 mL, 0.62 mg EuMac-di-NCS) was added with gentle shaking to a sample of polylysine HMTA solution. The mixture was allowed to stand at room temperature for 45 min, after which time 0.100 mL of $2.0\times10^{-2}$ M aspartic acid was added with gentle shaking. The mixture was allowed to stand at room temperature for an additional 15 min; it was then chromatographed through a column (17 cm height, 7 mm id) of SEPHADEX™ G-25 in 0.267M HMTA pH 7.5 buffer. Elution with the same HMTA buffer, using a flow-cell detector (D-Star Instruments, DFW-20 Fixed Wavelength Detector) set for absorbance at 280 nm (absorption of lysine-bound EuMac), gave the coupled peptide as a colorless solution. The eluate was divided into several portions. One portion was quantitatively analyzed for Eu by flame atomic absorption. Another portion was analyzed for polylysine by absorbance, using the Biuret technique. The third portion was analyzed for Eu-luminescence as follows: 0.100 mL of eluate, 0.400 mL of $5\times10^{-2}$ M HTTFA and 1.00 mL of a 0.71 M HMTA pH 6.0 were diluted with ethanol to 25.0 mL and the emission spectrum was obtained with excitation at 350 nm.
  (b) The procedure described in (a) was repeated using 5.3 mg of polylysine and 0.300 mL of the EuMac-di-NCS DMSO solution (1.23 mg EuMac-di-NCS).
  (c) The procedure described in (a) was repeated using 4.8 mg of polylysine and 0.470 mL of the EuMac-di-NCS DMSO solution (1.93 mg EuMac-di-NCS).

Figure 2:
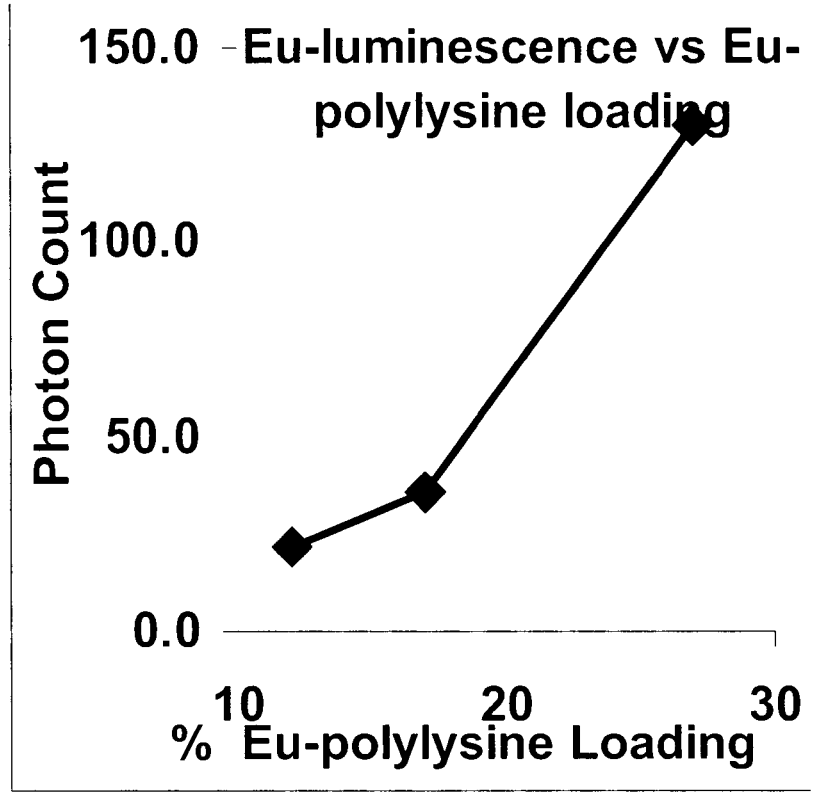
FIG. 2. Eu(III) emission at 618 nm normalized to $1 \times 10^{-6}$ mmol polylysine/mL, as a function of Eu-polylysine percentage loading.
Figure 3:
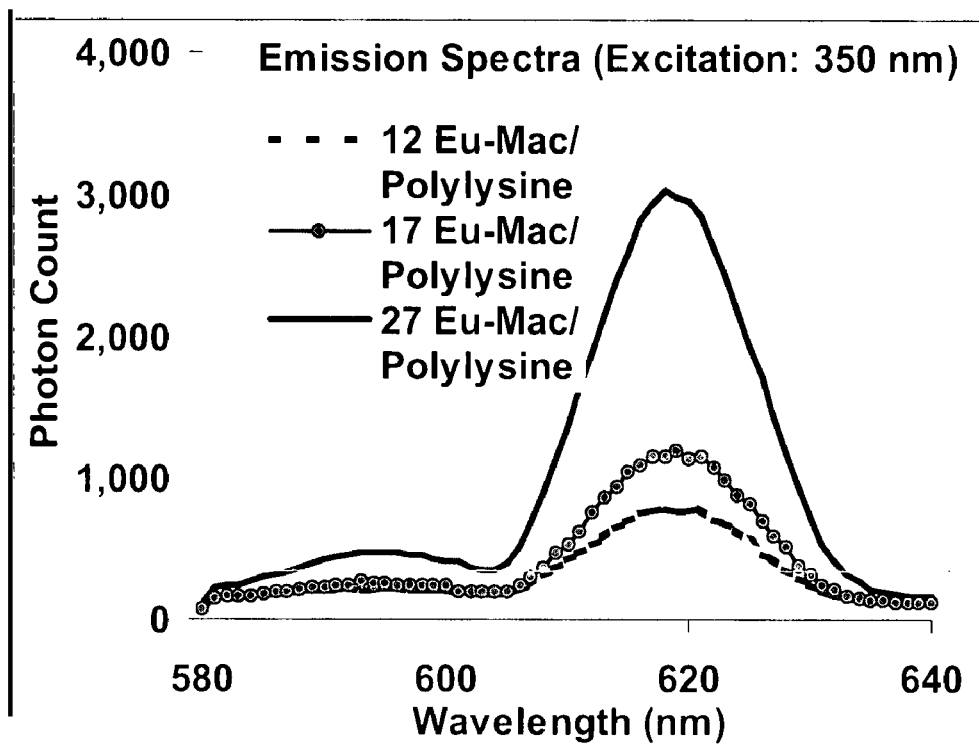
FIG. 3. Eu-Emission spectra of EuMac-polylysine conjugates at different Eu-polylysine percentage loadings.

The average yield of EuMac-coupled peptide in the three experiments was ca. 15% relative to the starting peptide. These experiments gave the following results, illustrated in FIG. 1, FIG. 2 and FIG. 3: (1) The average EuMac-to-polylysine mole ratio in the coupled peptide, referred to as Eu-polylysine loading in the following, increased proportionally to the Eu-polylysine mole ratio used in the coupling reaction. (2) The emitted photon count, when normalized to account for different peptide concentrations, increased proportionally to the Eu-peptide loading. (3) The emission spectra of EuMac-polylysine samples with different Eu-polylysine percentage loadings showed identical patterns, confirming that the emitting species are the same in each case.

Example II

Synthesis of a Luminescent Lysine-phenylalanine Copolymer with Side Chains Consisting of a Hexa-aza-macrocyclic Complex of Europium(III)

A. Materials
  (a) Lysine-phenylalanine (4:1) random copolymer (m.wt 47,200), SIGMA® Catalog No. P-3150 (Lysine-phenylalanine.)
  (b) Other materials as in Example I.
B. Procedure
  (a) The coupling and chromatography experiments described in Example I were repeated using a lysine-phenylalanine (4:1) random copolymer, with the flow detector set for absorbance at 250 nm (phenylalanine absorption). The following quantities were used for the coupling reactions:
    (i) Lysine-phenylalanine, 4.8 mg; EuMac-di-NCS, 0.566 mg; Eu/peptide reagents mole ratio=5.32.
    (ii) Lysine-phenylalanine, 5.3 mg; EuMac-di-NCS, 1.13 mg; Eu/peptide reagents mole ratio=9.67.
    (iii) Lysine-phenylalanine, 5.3 mg; EuMac-di-NCS, 1.81 mg; Eu/peptide reagents mole ratio=15.5.

TABLE 1

Comparison of the emission intensities (as normalized photon counts) of EuMac-poly-lysine-phenylalanine copolymers obtained with different Eu-to-peptide reagent ratio.

| Eu-Peptide Reagent Ratio | Normalized Photon Count |
|---|---|
| 5.32 | $4.69 \times 10^8$ |
| 9.67 | $6.03 \times 10^8$ |
| 15.5 | $7.9 \times 10^8$ |

Figure 4:
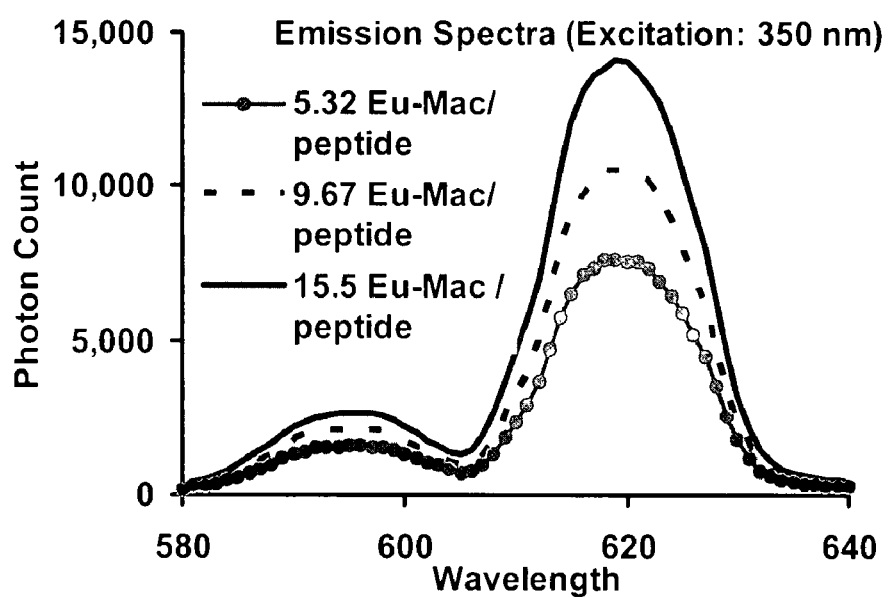
FIG. 4. Eu-Emission spectra of EuMac-Polylysine-phenylalanine conjugates as a function of different EuMacNCS/poly-lysine-phenylalanine ratios used in the coupling reactions.

(b) The average yield of coupling-elution was ca. 18% relative to initial peptide. The eluates were analyzed for peptide using the BIO-RAD Protein Assay technique (Bio-Rad Laboratories, Inc., US/EG Bulletin 1069), and for Eu-luminescence as described in Example I. The results, summarized in Table I and FIG. 4, showed that the normalized Eu-luminescence increased proportionally to the Eu/peptide reagent mole ratio.

Example III

Synthesis of a Luminescent Lysine-Tryptophan Copolymer with Side Chains Consisting of a Hexa-aza-macrocyclic Complex of Europium(III)

A. Materials
  (a) Lysine-tryptophan (4:1) random copolymer (m.wt. 38,000) SIGMA® Catalog No. P-9285, (Lysine-tryptophan).
  (b) Other materials as in Example I.
B. Procedure
  (a) The coupling and chromatography experiments described in Example I were repeated using a lysine-tryptophan copolymer, with the flow detector set for absorbance at 280 nm (tryptophan and EuMac absorptions). The following quantities were used for the coupling reactions:
    (i) Lysine-tryptophan, 4.9 mg; EuMac-di-NCS, 0.4 mg; Eu/peptide reagents mole ratio=3.26.
    (ii) Lysine-tryptophan, 4.9 mg; EuMac-di-NCS, 0.8 mg; Eu/peptide reagents mole ratio=6.51.

TABLE 2

Comparison of the emission intensities (as normalized photon counts) of EuMac-lysine-tryptophan copolymers obtained from different Eu-to-peptide reagentratios.

| Eu-Peptide Reagent Ratio | Normalized Photon Count |
|---|---|
| 3.26 | $8.5 \times 10^7$ |
| 6.51 | $34 \times 10^7$ |

A precipitate formed during the coupling reactions and the solutions were filtered prior to chromatography. The average yield of Eu-coupled peptide was less than 10% relative to the initial peptide. The eluates were analyzed for peptide by absorbance at 282 nm and for Eu-luminescence as described in Example I. The results, summarized in Table 2, showed a regular increase in Eu-peptide loading with increasing Eu/peptide reagent mole ratio.

The combined results of Example I, Example II, and Example III clearly demonstrate that the polymer bound EuMac does not concentration quench and therefore the use of EuMac and other lanthanide optical-labels attached to a polymer is both scientifically and commercially feasible.

Example IV

Selective Cleavage and Release (pH 7.1) of a Peptide Containing Amino Acids Capable of Forming Both Covalent Bonds with a Functionalized Dye and Forming Conjugates with a Member of a Specific Combining Pair A. Materials:
(a) The Proteinase K cleavable peptide shown in Formula XI was synthesized on a Merrifield synthesizer by a commercial vendor, ANASPEC Inc. San Jose, Calif. (Peptide Name: NIRL-2) following standard commercial procedures, which are similar to those described by Peterson and Meares (Ref. 9). The carboxyl of the first amino acid, alanine, was covalently bonded to the amino functionalized version of the solid support, Polymer Laboratories, PL-PEGA Resin.

Formula XI shows a Proteinase K cleavable peptide bound to a PL-PEGA Resin bead. This structure shall be referred to as Peptide-PEGA-Bead(s). The peptide of Formula XI contains ProAla-ProPhe(Ala)$_3$, which is peptide VII of Table III of Bromme et al. 1986 (Ref. 38). Peptide VII has the highest ratio, 133,000 sec.$^{-1}$ mole$^{-1}$, between the rate of catalysis and the Michaelis constant. Bromme et al. (Ref. 38) describe this ratio as a measurement of protease activity.

Formula XI

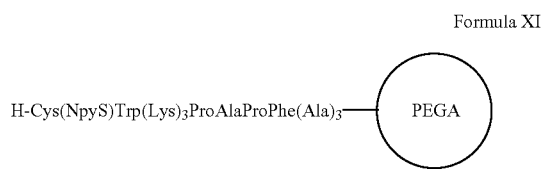

H-Cys(NpyS)Trp(Lys)$_3$ProAlaProPhe(Ala)$_3$—PEGA

The Peptide of Formula XI includes 3 lysines, which can react with an isothiocyanate or other reactive functionality, such as those present on functionalized optical-labels. The 3-nitro-2-pyridine-sulfenyl (NpyS) group is bound to the cysteine by a disulfide link which can subsequently undergo a disulfide exchange with an available cysteine or other sulfhydryl of an analyte-binding species, analyte, or member of a specific combining pair, such as an antibody. According to Mezö et al. 2000 (Ref. 39), the exchange with the antibody should be favored.

(b) Aqueous solution containing TRIS (0.01 M) and CaCl$_2$ (0.001 M) adjusted to pH-7.07 with 10N and ca. 0.4N NaOH and with 12N and ca. 0.5N HCl, (Tris-Ca Buffer).
(c) The Proteinase K was diluted 100th fold with distilled water to reach 230 μg/mL; 10 μL of the 23 mg/ml stock solution with 990 μL of distilled water (Proteinase K).

B. Procedure
(a) The experiment, as described in Table 3, involved two samples: Control and 15.1 μg/mL of Proteinase K. The two samples of Peptide-PEGA-Beads were weighed in 1.5 mL EPPENDORF TUBES.
(b) In order to maximize the sensitivity and precision of the measurement of the enzymatic hydrolysis, the contamination by free peptide was minimized. The Peptide-PEGA-Beads were first washed by adding 200 μL of Tris-Ca Buffer, followed by vortex-mixing for one minute (Wash 1). The Peptide-PEGA-Beads were allowed to settle by gravity and the supernatant was removed with a 200 μL tip PIPETMAN. A second 200 μL of Tris-Ca Buffer was added to the Peptide-PEGA-Beads, which were allowed to stay in the buffer 1.2 hours (Wash 2). A 90 μL aliquot was removed from both washes with a 200 μL tip PIPETMAN. All operations were performed at room temperature, approximately 25° C.
(c) 800 μL of Tris-Ca Buffer was added to the Peptide-PEGA-Beads, which were then vortex-mixed for a few seconds. The Peptide-PEGA-Beads were allowed to settle by gravity and subsequently a 90 μL aliquot was removed with a 200 μL tip PIPETMAN, (0 min. pre-addition sample).
(d) The two washes and the 0 min. pre-addition sample from the Peptide-PEGA-Bead sample were subsequently transferred to 40 μL cuvettes and the absorbance spectrum was obtained with a spectrophotometer.

TABLE 3

Enzymatic Hydrolysis Conditions

| Experimental Conditions | Beads (mg) | Final Prot-K (μg/mL) | Buffer (μL) | Prot-K (μg) | Prot-K stock (μL) | dH$_2$O (μL) | Total Vol. (μL) |
|---|---|---|---|---|---|---|---|
| Control | 1.4 | 0 | 710 | 0 | 0 | 50 | 760 |
| 15.1 Prot-K | 1.4 | 15.1 | 710 | 11.5 | 50 | 0 | 760 |

Figure 5:
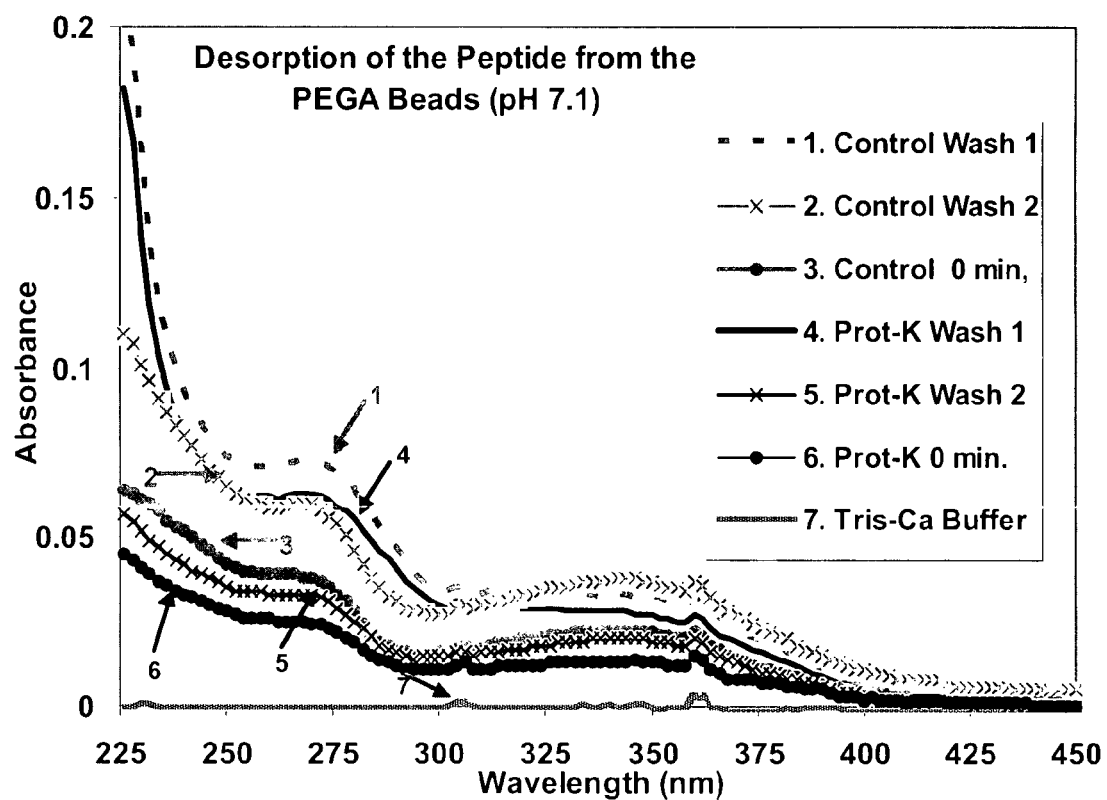
FIG. 5. Desorption of the peptide of Formula XI from the Peptide-PEGA-Beads. The absorbance peaks at ca. 275 and at ca. 340 nm arise from the tryptophan residue and the NpyS, respectively. At this point in the experiment, which is prior to the addition of Proteinase K, both the Control and the Proteinase K samples are essentially identical except for a small difference in the amount of Peptide-PEGA-Beads.
Figure 6:
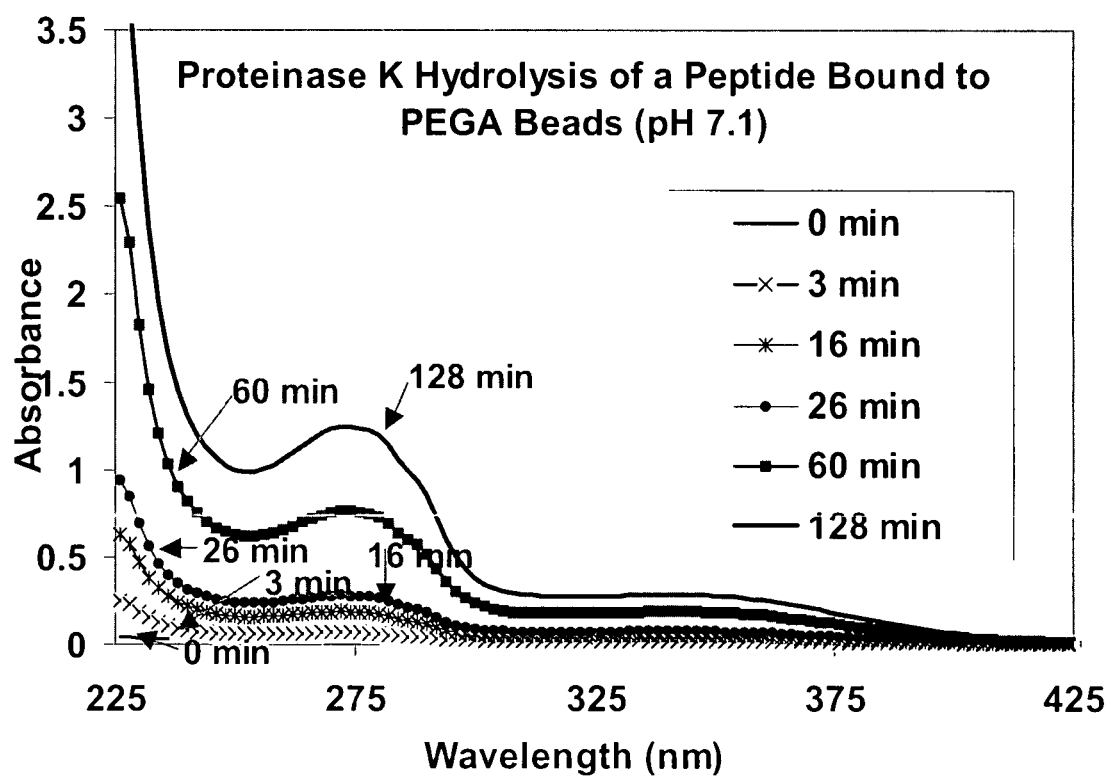
FIG. 6. Proteinase K (15.1 µg/mL) hydrolysis at pH 7.1 of the Peptide-PEGA-Beads (1.4 mg). The spectra indicates that, with time, Proteinase K cleaves the peptide from the solid support and that the released peptide includes both tryptophan and NpyS.
Figure 7:
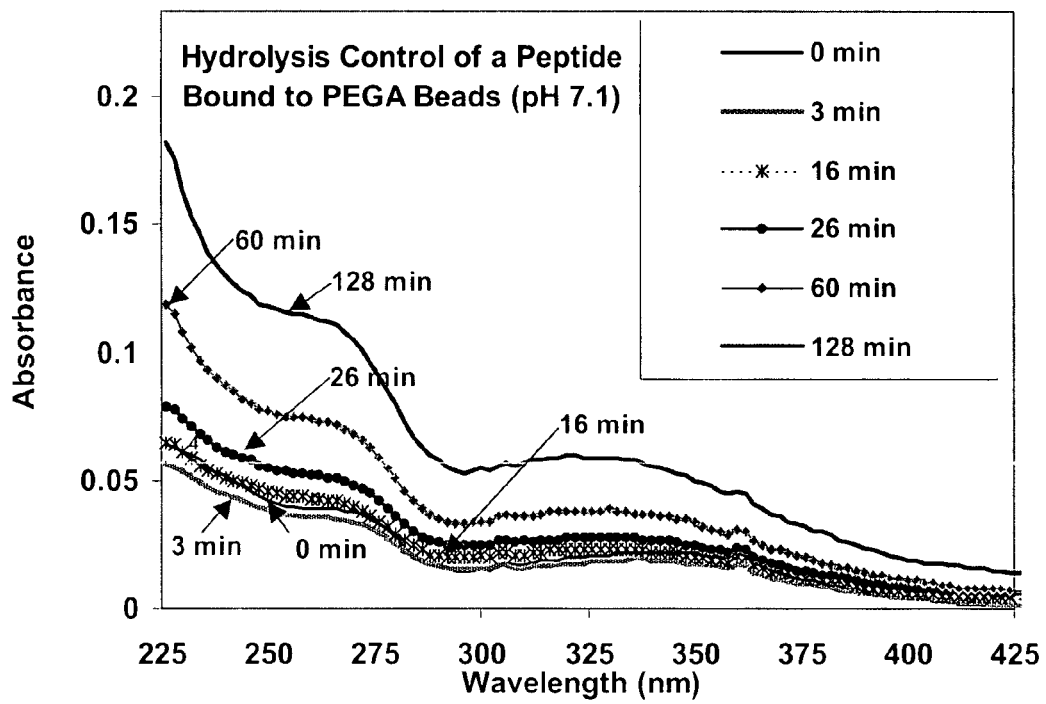
FIG. 7. Hydrolysis (pH 7.1) of the Control sample of Peptide-PEGA-Beads (1.4 mg). These spectra indicates that, with time, the peptide is slowly going into solution. Note that the ordinate scale is one fifteenth relative to that of FIG. 6. No Proteinase K was present.

(e) As shown in FIG. 5, some of the peptide was washed off of the Peptide-PEGA-Beads prior to the addition of the Proteinase K. For both samples, the wash of the dry Peptide-PEGA-Beads, Wash 1, resulted in the largest loss of peptide (highest absorbance). The second wash, Wash 2, showed a smaller loss, and the 0 min pre-addition sample, which is equivalent to a third wash, showed an even lower loss.
(f) Proteinase K (0 and 11.5 μg) was added to the two washed samples of Peptide-PEGA-beads, the total volume was brought up to 760 μL with Tris-Ca Buffer and water, and at selected times 90 μL aliquots of supernatant were obtained from the settled beads as described in (c).
(g) The aliquots of supernatant were transferred to a 40 μL cuvette and the absorbance spectra were obtained with a spectrophotometer.
(h) The data for the 0 min. pre-addition samples were also included as reference.
(i) After the addition of Proteinase K, the absorbance of the supernatants from both the Proteinase K sample and the Control sample increased above that of the respective O-min pre-addition supernatants (FIG. 6 and FIG. 7). The supernatants from both the Proteinase K and the Control samples showed the 275 nm and 350 urn peaks characteristic of tryptophan and NpyS. However, the release of the free peptide was much greater for the Proteinase K sample.

Figure 8:
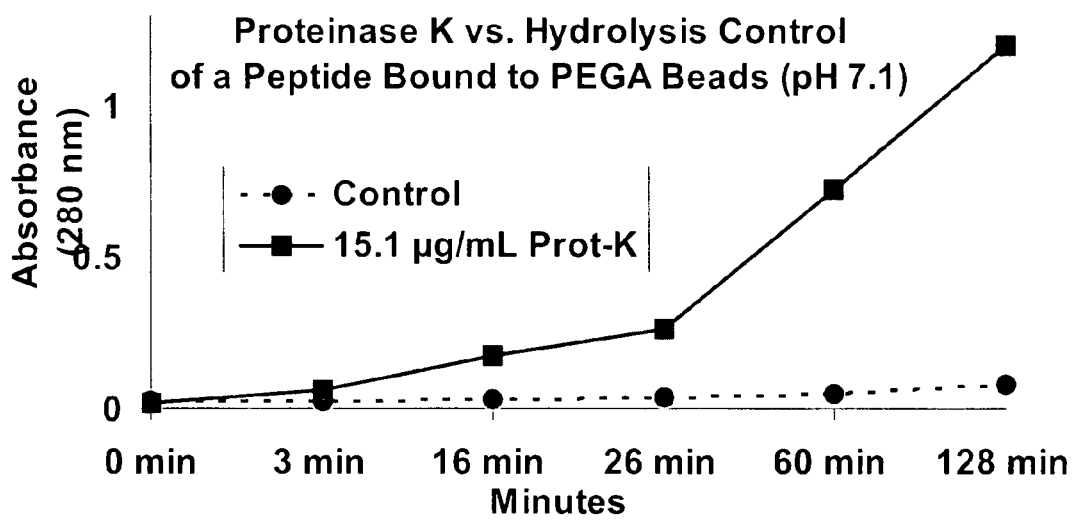
FIG. 8. Graph of the absorbance of the supernatants for the Control and Proteinase K 15.1 µg/mL samples at 280 nm.

As shown in FIG. 8, the increase in absorbance of the supernatants of the Control sample was negligible compared to that of the supernatants of the Proteinase K sample. No appreciable amount of peptide was released spontaneously within the time required for significant cleavage of the peptide by Proteinase K.

Example V

Selective Cleavage and Release (pH 8.0) of a Peptide Containing Amino Acids Capable of Both Forming Covalent Bonds with a Functionalized Dye and Forming Conjugates with a Member of a Specific Combining Pair A. Materials:
   (a) The Tris-Ca Buffer of Example IV adjusted to pH 8.01 with 10N and ca. 0.4N NaOH and with 12N and ca. 0.5N HCl.
   (b) All other materials as described in Example IV.

TABLE 4

Enzymatic Hydrolysis Conditions

| Experimental Beads Conditions | Final Beads (mg) | Buffer Prot-K (μg/mL) | Prot-K (μL) | Prot-K (μg) | Prot-K stock (μL) | H$_2$O (μL) | Final Vol. (μL) |
|---|---|---|---|---|---|---|---|
| Control | 1.2 | 0 | 710 | 0 | 0 | 100 | 810 |
| 14.2 Prot-K | 1.1 | 14.2 | 710 | 11.5 | 50 | 50 | 810 |
| 28.4 Prot-K | 1.1 | 28.4 | 710 | 23 | 100 | 0 | 810 |

Figure 9:
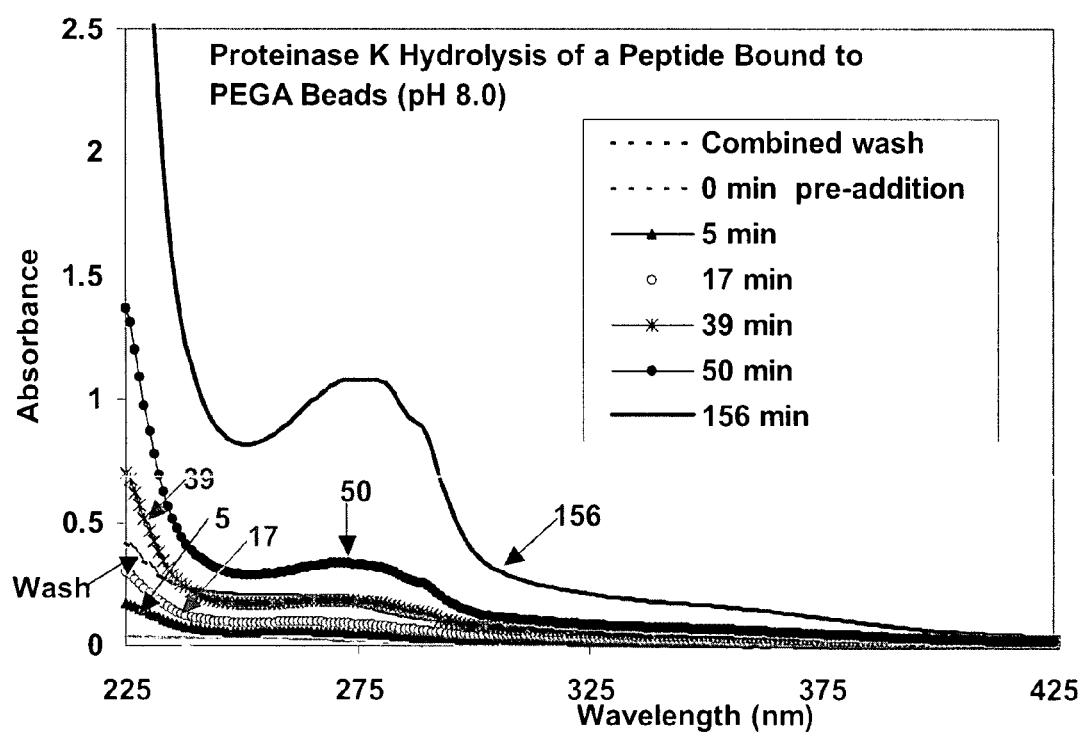
FIG. 9. Proteinase K (14.2 µg/mL) hydrolysis at pH 8.01 of the Peptide-PEGA-Beads (1.1 mg). The spectra indicate that with time (5 to 156 min), Proteinase K cleaves the peptide, and that the released peptide includes both tryptophan and NpyS. A small amount of the Peptide bound to the Peptide-PEGA-Beads is initially washed oft (Combined Wash). The preaddition, 0-min sample shows minimal background. At pH 8 the NpyS absorbance at 350 nm is reduced.

B. Procedure:
   (a) The experiment, as summarized in Table 4, involved three samples: Control, 14.2 ug/mL Proteinase K and 28.4 ug/mL Proteinase K. The Peptide-PEGA-Beads were weighed in 1.5 mL Eppendorf Tubes
   (b) The procedures of Example IV were followed, with the exceptions that the hydrolysis was carried out at pH 8.01, two concentrations of Proteinase K were studied, and Wash 1 and Wash 2 were combined.
   (c) After the addition of 14.2 μg/mL of Proteinase K, the absorbance of the supernatants increased with time as illustrated in FIG. 9. Similar spectra (not shown) were obtained for the sample treated with 28.4 μg of Proteinase K. Both the spectra at 156 min (FIG. 10) and the change of absorbance with time (FIG. 11) demonstrate that Proteinase K cleaves a peptide from the Peptide-PEGA-Beads. The concentration of the peptide thus cleaved is much greater than that present in the supernatant of the Control sample or in any of the three Combined Washes. The doubling, of the enzyme concentration resulted in an approximately 1.3 fold increase in cleaved peptide (FIG. 11).

Figure 10:
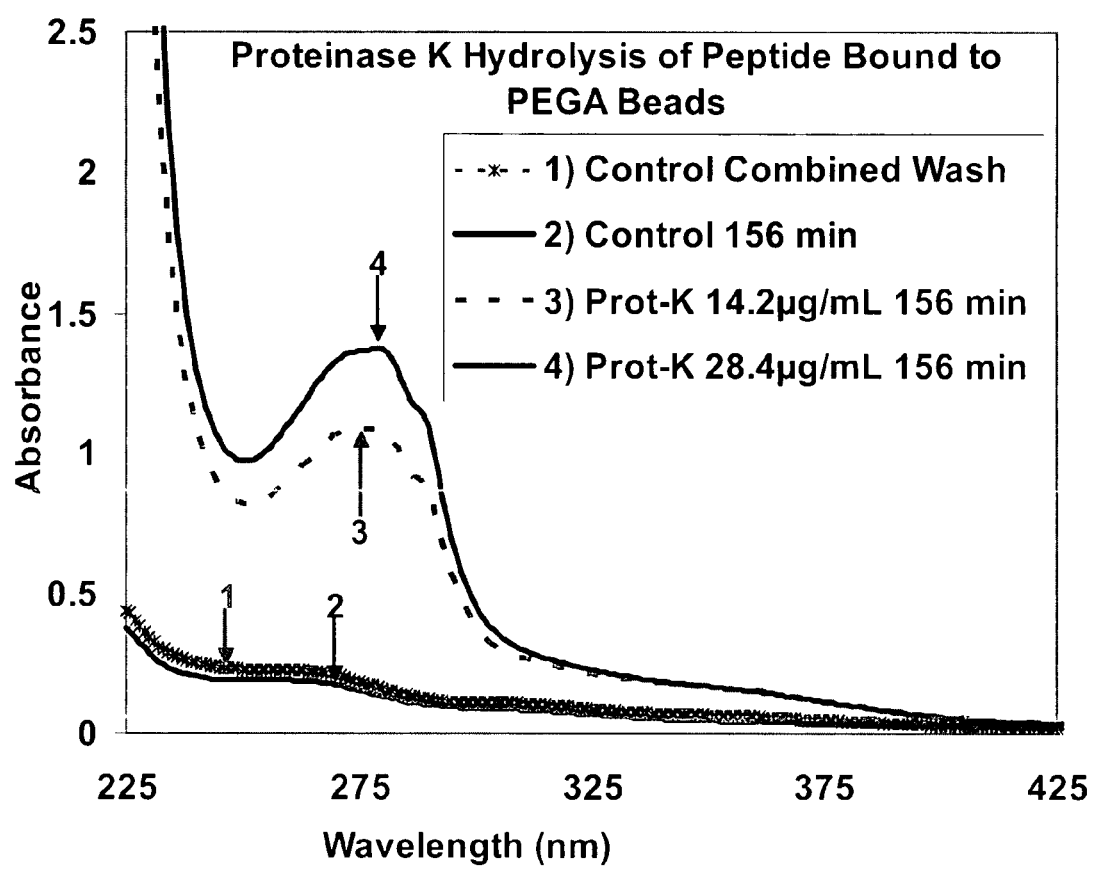
FIG. 10. The Combined Washes of the two Proteinase K samples (not shown) were essentially the same as the one from the Control. The spectra indicate that, after 156 min, both concentrations of Proteinase K cleave the peptide from the solid support. All four spectra show a clear tryptophan peak at 275-280 nm.
Figure 11:
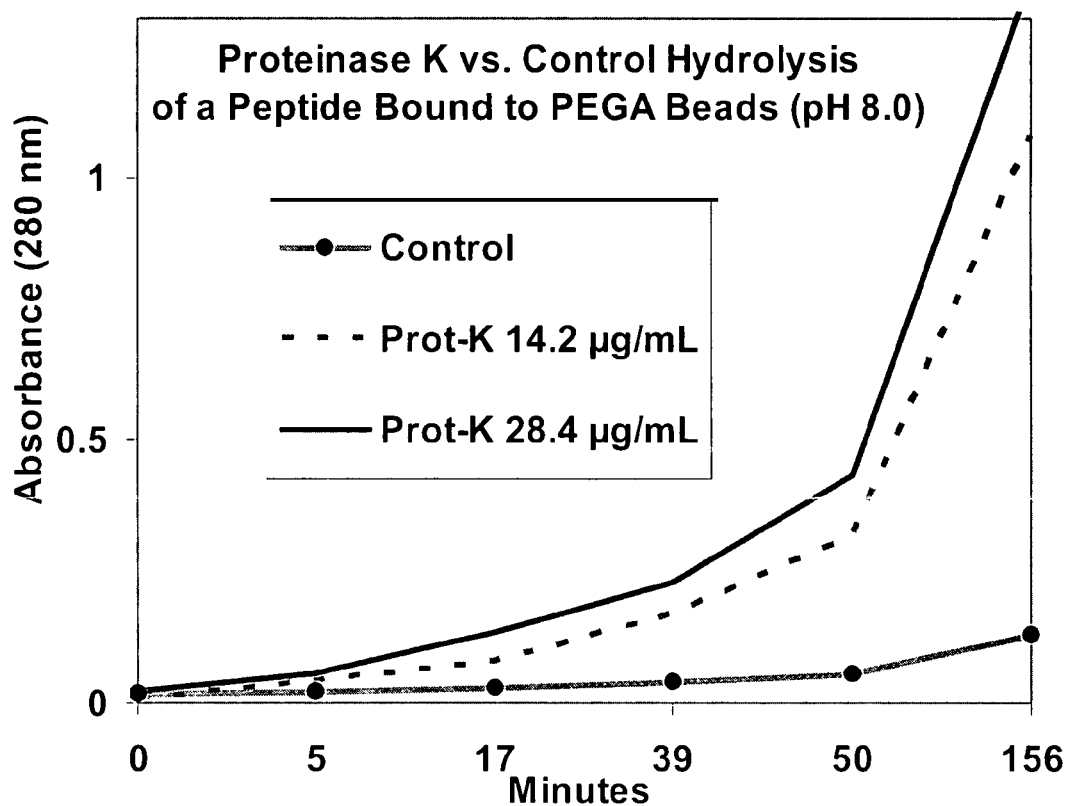
FIG. 11. The graph shows how the absorbance at 280 nm of the supernatants from the Control sample and of the Proteinase K 14.2 and 28.4 µg/mL samples increases with time. The ratio of released peptide for the 28.4 vs. 14.2 µg/mL is approximately 1.3.

Both the supernatants from the Proteinase K samples and the Control sample showed the 275 nm peak due to tryptophan absorption (FIG. 10). However, the 350 nm peak from the NpyS that was observed at pH 7.1 is no longer discernible.

Example VI

Demonstration of the Resistance of a Monoclonal Antibody to Proteinase K Digestion A. Materials
   (a) The Tris-Ca Buffer of Example V adjusted to pH 8.06.
   (b) PRB-1, an antibody specific for the 5BrdU marker for DNA (Anti5BrdU) and labeled with a fluorescein analog, available from Phoenix Flow Systems, Catalog No. ABFM18, San Diego, California.
   (c) The containers used for the experiment were Fisher 5 mL polystyrene round bottom tubes, 12×75 mm style, FISHER SCIENTIFIC Catalog No. 2008.
   (d) The reagents in the Phoenix Flow APO-BRDU™ kit, Catalog No: AU1001, were used for the measurements.

B. Procedure

The resistance of labeled Anti5BrdU to Proteinase K was demonstrated by the use of this anti-body in the measurement of apoptosis, employing commercial flow cytometry reagents and procedures. A comparison was made between the antibody before and after enzymatic digestion with two concentrations of Proteinase K. Apoptosis results in DNA strand breaks terminated by 3'-hydroxyl ends. In the absence of a template, terminal deoxytransferase, TdT, adds nucleotides to these ends including the analog BrdUTP. The Phoenix Flow kit included an Anti5BRdU coupled to a 488 nm excited fluorescent dye. The Anti5BrdU binds to the incorporated BrdU. The Propidium iodide/RNase solution from the APO-BRDUT™ kit was used according to the manufacturer's instructions to specifically stain the total DNA.

(a) Proteinase K was diluted with the pH 8.08 Tris-Ca Buffer to concentrations of 24 and 240 μg/mL. The Anti5BrdU was diluted to 0.1 μg/uL with the pH 8.01 Tris-Ca Buffer, according to the published instructions. Proteinase K was added and the samples were incubated at room temperature for 58 min.
   (b) Within less than 5 minutes after the end of the incubation, one mL, 1.0×10$^6$ cells, of previously prepared BrdUrd labeled control cells were added to a mixture of 90 uL of Rinse Buffer of the Phoenix Flow kit and 10 uL of the Anti5BrdU solution. The cells with the labeled Anti5BrdU solution were incubated in the dark for 30 minutes at room temperature. 0.5 mL of the Propidium Iodide/RNase A Solution was added to stain the DNA. The 5 mL tubes were wrapped with aluminum foil and the cells were incubated in the dark for 30 minutes at room temperature.
   (c) After incubation, a FACScan (Becton Dickenson) flow cytometer equipped with a 488 nm laser and logarithmic amplifiers was used to measure the cells fluorescence arising from both the fluorescein analog labeled Anti5BrdU and the Propidium Iodide.
   (d) The results shown in Table 5 demonstrated that 24 μg/mL of Proteinase K had negligible effect on the antibody and that even after exposure to a 10 times greater Proteinase K concentration, 65% of the positive cells could still be detected. For the 0 (control), 24, and 240 μg/mL Proteinase K treatments, the differences between the positive and negative channels were 440, 432, and 289 respectively. Note that a concentration of 24 μg/mL is approximately equal to the 28.4 μg/mL concentration and twice the 14.2 μg/mL concentration used in Example V (Table 4). Thus, a significant amount of biologically active antibody survived the enzymatic hydrolysis condition of the peptide of Example IV and Example V.

TABLE 5

Effect of Proteinase K Treatment on Anti5BrdU

| Prot-K (μg/mL) | Anti-5BrdU μg/μL | % Fluor. Cells | Mean Channel of Pos. Cells | Mean Channel of Neg. Cells | Pos. - Neg. Mean Channel |
|---|---|---|---|---|---|
| 0 | 0.1 | 36.7 | 675 | 235 | 440 |
| 24 | 0.1 | 35.5 | 681 | 249 | 432 |
| 240 | 0.1 | 24.0 | 524 | 235 | 289 |

Example VII

Coupling of a Functionalized Europium Macrocycle to the PEGA Bound Peptide of Example IV and Release of the Europium Macrocycle Labeled Peptide by Enzymatic Hydrolysis A. Materials
  (a) Dimethylsulfoxide (DMSO) ACS Reagent, SIGMA® Catalog No. D-8779.
  (b) EuMac-mono-NCS in DMSO solution ($5.4 \times 10^{-3}$ M, 4.6 mg/mL).
  (c) The Peptide-PEGA-Beads, Formula XI of Example IV A (a).
  (d) HMTA 0.267 M solution in water, adjusted to pH 9.45 with NaOH (0.267 M HMTA pH 9.45 buffer).
  (e) HMTA 0.267 M solution in water, adjusted to pH 7.5 with HCl (0.267 M HMTA pH 7.55 buffer).
  (f) Tris-Ca Buffer adjusted to pH 8.0 with 1M HCl (Tris-Ca pH 8.0 buffer).
  (g) Proteinase K 0.46 µg/µL in Tris-Ca pH 8.06 buffer (Proteinase K solution).
  (h) Cofluorescence solution prepared with $GdCl_3 \cdot 6H_2O$ (99.99%), ALFA AESAR®, Catalog No. 11287 (1999).

B. Procedure
  (a) 2.3 mg of the Peptide-PEGA-Beads were weighed in a 1.5 mL EPPENDORF TUBE.
  (b) A mixture consisting of 0.20 mL of DMSO and 0.50 mL of the 0.267 M HMTA pH 9.45 buffer was added to the Peptide-PEGA-Beads, which were then dispersed by vortex-mixing for approximately 2 minutes. The EuMac-mono-NCS solution (0.150 mL, 0.69 mg EuMac-mono-NCS) was slowly added with gentle tapping to suspend the Peptide-PEGA-Beads. The total volume was 850 uL.
  (c) The Peptide-PEGA-Beads were allowed to stand at room temperature for 45 min and allowed to settle by gravity. Subsequently the buffer was removed with a 200 uL tip PIPETMAN.
  (d) Step (b) was repeated.
  (e) Step (c) was repeated except that the Peptide-PEGA-Beads Were allowed to stand at room temperature for 53 nun.
  (f) The Peptide-PEGA-Beads were then washed four times with 150 uL of HMTA pH 7.55 buffer. This washing restored the EuMac to neutrality and removed contaminants, such as any unbound EuMac-mono-NCS. Formula XII shows the Peptide-PEGA-Beads with EuMac bound to the lysine residues. The position and number of the EuMac in Formula XII is diagrammatic. The number of EuMacs bound on each peptide ranged from 0 up to 3. This structure shall be referred to as EuMac-Peptide-PEGA beads.
  (g) The EuMac-Peptide-PEGA-Beads can be stored at this time in either dimethylformamide or ethanol at −20° C. or below.

Formula XII

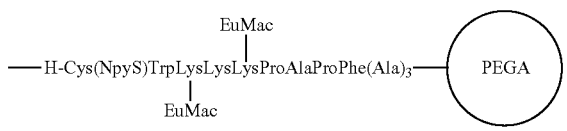

Figure 12:
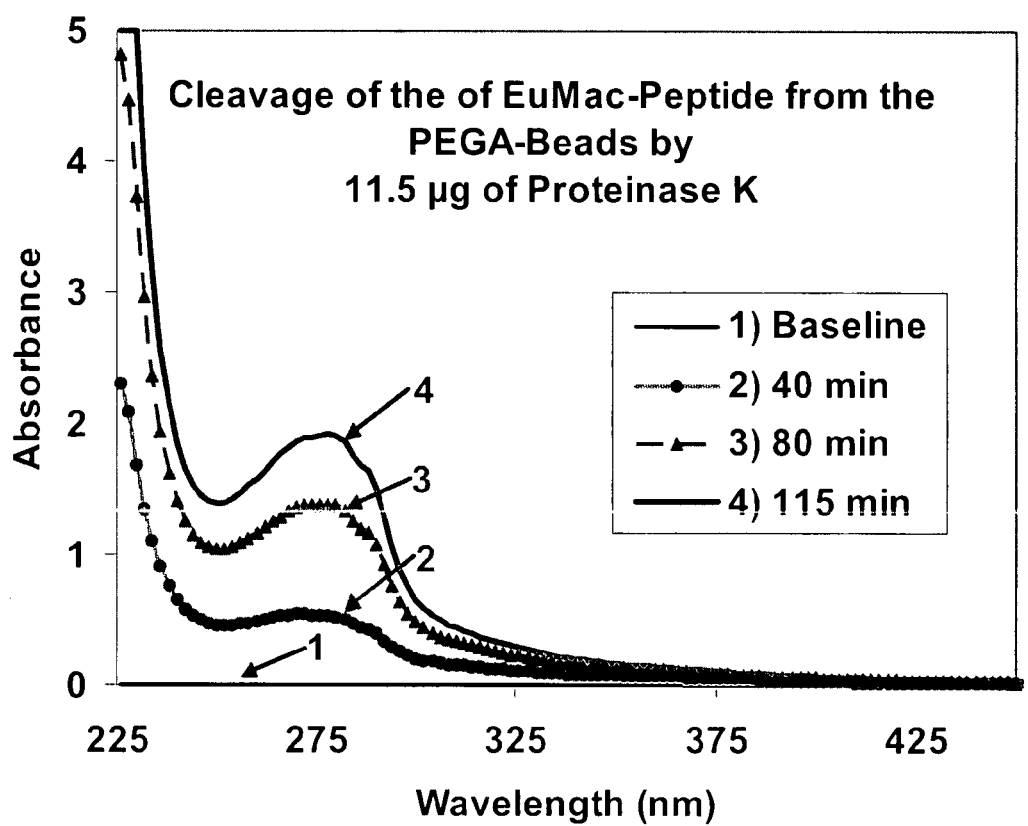
FIG. 12. Graph of supernatant from Proteinase K hydrolysis of EuMac-mono-NCS and NIRL-2 beads conjugate. The graph shows that the absorbance at about 280 nm increases with time for all samples. The longer the hydrolysis time, the higher the absorbance results at about 280 nm. This demonstrates that Proteinase K cleaves the peptide from the PEGA-Beads.

(h) The Peptide-PEGA-Beads were then washed two times with 150 µL of Tris-Ca pH 8.0 buffer and finally suspended with 426 µL of Tris-Ca pH 8.0 buffer.
  (i) The Proteinase K solution (25 µL, 11.5 µg) was then added to the EuMac-Peptide-PEGA Beads resulting in a total volume 451 µL and a Proteinase K concentration of 25.5 µg/mL.
  (j) The EuMac-Peptide-PEGA-Beads were allowed to settle for approximately one minute, 70 µL aliquots of the supernatant were removed at 40, 80, 115, and 124 minutes using a 200 µL tip PIPETMAN, and the absorbance spectra were obtained with a spectrophotometer employing 40 µL cuvettes.
  (k) The increasing absorbance readings at 280 nm, shown in FIG. 12, indicate that the Proteinase K did release a cleavage product containing tryptophan from the EuMac-Peptide-PEGA-Beads.
  (l) All EuMac-Peptide-PEGA-Bead samples were stored at 8° C. Small samples of beads were mixed with the cofluorescence solution for observation with an episcopic fluorescence microscope equipped with a 10× objective 0.25 N.A. The UV illumination was provided by a 100 watt Mercury-Xenon short are. The fluorescence was excited at 365 nm and the emitted light was observed through an OMEGA® Optical PloemoPak cube, UV DAPI, equipped with the following: a 365 rim narrow-band-width excitation filter (OMEGA® 365HT25), a 400 nm Beamsplitter (OMEGA® 400DCLP02), and a two-band 450 and above 600 nm emission filter (OMEGA® 450DF65). The CCD optical path was equipped with a 619 nm narrow-band, 5.6 half-width, emission filter (OMEGA® 618.6NB5.6). The images were obtained with an uncooled EDC-1000N CCD camera (652×494). The gray levels of the images were inverted for display. Darkness indicates strong luminescence.

Figure 13:
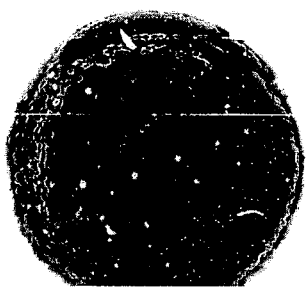
FIG. 13. CCD Images (619 nm emission) of a EuMac-Peptide-PEGA-Beads with added cofluorescence solution, before hydrolysis with Proteinase K (Left) and after 115 minutes of hydrolysis (Right). The exposure was 500 ms with a 10×, N.A 0.25 objective. The bead on the left luminesces much more strongly than the two beads on the right. The white spots on the bead on the left are pixel artifacts.

Both the pre-hydrolysis sample of the EuMac-Peptide-PEGA-Beads and the sample hydrolyzed for 115 min fluoresced under UV excitation (FIG. 13). However, the luminescence from the pre-hydrolysis sample was strong and the luminescence from the sample hydrolyzed for 115 min was weak. The strong luminescence demonstrated that significant amount of EuMac had coupled to the peptide. The drastic difference in luminescence before and after Proteinase K hydrolysis demonstrated that the EuMac-labeled part of the peptide was released from the bead.

The periphery of the pre-hydrolysis sample bead also had luminescence, but this was not as bright as that of the bead itself (FIG. 13 Left). A reasonable explanation for this luminescence "halo" from the solution immediately surrounding the pre-hydrolysis bead is that it results from the EuMac-Peptide attached to the polyethylene glycol pendant polymer side chains that emanate from the PEGA-BEAD. The amount of EuMac-Peptide contained in this halo could have been considerable because the image observed through a microscope is a two-dimensional section of a three-dimensional object. To test for luminescence in the supernatant, a spot-test was performed by placing 2 uL of the hydrolyzed supernatant sample (115 minutes into the hydrolysis) on a slide with 2 uL of the cofluorescence solution; the spot did luminesce when irradiated at approximately 365 nm.

Combining the results of Example IV to Example VII proves that it is feasible to prepare peptides with an enzyme-cleavable site, conjugate the peptide with an optical-tag, in this case a lanthanide(III) macrocycle, and to enzymatically cleave the conjugated peptide from its support under condi-

Example VIII

Conjugation of an Antibody with the Europium Macrocycle Labeled PEGA-Bound Peptide of Example VII In this Example, an antibody is coupled to a PEGA-bound peptide. This procedure is based on G. T. Hermanson 1996 (Ref. 26) Chapter 10. Antibody Modification and Conjugation p. 456. The antibody is first selectively reduced to provide two half-molecules, each containing a cysteine, and then this cysteine replaces by disulfide exchange the NpyS group that was part of the PEGA-bound peptide.

A. Materials
- (a) The europium-macrocycle-labeled-peptide bound to PEGA beads of Example VII (EuMac-Peptide-PEGA Beads).
- (b) Unconjugated PRB-1 from Phoenix Flow Systems (Anti5BrdU).
- (c) EDTA, disodium salt dihydrate, molecular biology grade, SIGMA®, Catalog No. E5134 (2000-2001).
- (d) An aqueous solution containing $NaH_2PO_4$ (0.1 M), NaCl (0.15 M), and EDTA (10 mM) is titrated with an aqueous solution containing $Na_2HPO_4$ (0.1 M), NaCl (0.15 M), and EDTA (10 mM) to achieve pH 6.0 (Phosphate-EDTA-pH 6.0 buffer).
- (e) An aqueous solution containing HMTA (0.267 M) and NaCl is (0.15 M), adjusted to pH 7.2 with HCl. Dissolved oxygen is removed from the solution by bubbling nitrogen gas through it (anaerobic chromatography pH 7.2 buffer). The use of this buffer avoids exposure of the lanthanide(III)-macrocycle to either EDTA or phosphate.
- (f) 2-mercaptoethylamine HCl, PIERCE, Catalog, No. 20408 (2000).
- (g) Tris-Ca Buffer of Example IV.

B. Procedure
- (a) A chromatography column of SEPHADEX™ G-25 is equilibrated with anaerobic chromatography pH 7.2 buffer at 4° C.
- (b) Ten mg of the Anti5BrdU is added to 1 mL of Phosphate-EDTA-pH 6.0 buffer. 2-mercapto-ethylamine-.HCl (6 mg) is then added to the Anti5BrdU-containing solution and the mixture is vortex-mixed and incubated for 90 min at 37° C.
- (c) The solution containing the reduced Anti5BrdU half molecules with free sulfhydryl groups is added under anaerobic conditions to a SEPHADEX™ G-25 column (volume ratio of 1 to 20). This size exclusion chromatography separates the Anti5BrdU from the other components of the reducing solution without reoxidation of the cysteine. The effluent of the column is monitored at 280 nm and the first fractions, which contain the antibody, are pooled.
- (d) EuMac-Peptide-PEGA Beads are added to a test tube containing a magnetic stirrer. An aliquot of the pooled fractions from (c) containing reduced antibody halves in quantity to provide 5 sulfhydryls per NpyS of conjugated peptide is added to the EuMac-Peptide-PEGA Beads. The mixture is allowed to react for 20 hours at 4° C. with stirring under nitrogen, to form the Anti5BrdU-EuMac-Peptide-PEGA conjugate. The reduced antibody half liberates the S-Npys protecting group from the EuMac-Peptide-PEGA and forms a cystine disulfide bridge. The Peptide-PEGA-Beads are now linked to the antibody by the intervening peptide, Formula XIII. The free 3-nitro-Pyridine-2-thione is incapable of participating in further mixed disulfide formation (Hermanson Chapter 2, 1996 (Ref. 26) p. 151.
- (e) The suspension of the Anti5BrdU-EuMac-Peptide-PEGA conjugate beads is centrifuged at 200×g for five minutes at 4° C. and the supernatant is removed. The removal of the supernatant minimizes contaminants, such as unbound antibody and free 3-nitro-Pyridine-2-thione.
- (f) Tris-Ca Buffer is added to the centrifuge tube of step (e) in the ratio of 0.8 mL per 1 mg of beads and the beads are suspended by tapping. The contents are again centrifuged at 200×g for five minutes and the supernatant is removed. The wash with Tris-Ca Buffer is repeated; another aliquot of Tris-Ca Buffer containing 40% glycerol is added and the beads are stored at −20° C. The structure of the conjugate of Anti5BrdU with the EuMac-Peptide-PEGA is shown by the schematic Formula XIII:

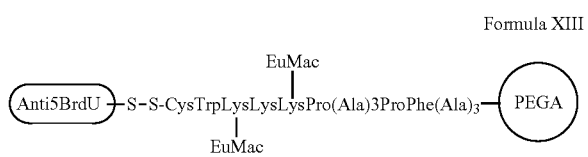

Formula XIII

The structure of Formula XIII shall be referred to as Anti5BrdU-EuMac-Peptide-PEGA Conjugate beads

Example IX

Enzymatic Cleavage of the Antibody Conjugate of the Europium Macrocycle Peptide of Example VIII from the PEGA Beads A. Materials
- (a) The Anti5BrdU-EuMac-Peptide-PEGA Conjugate beads of Example VIII, previously washed and suspended and washed in Tris-Ca Buffer.
- (b) HMTA buffer (0.267 M) adjusted to pH 7.5 with HCl (0.267 M HMTA pH 7.5 Buffer).
- (c) MICROCON® YM-10 Centrifugal ultrafiltration unit with an ultrafilter fabricated from regenerated cellulose with a molecular weight cut-off of 10,000 daltons. MILLIPORE, Catalog No. 42407, (10,000 mw cut-off filter).

B. Procedure
- (a) The procedures of Example IV and Example VII are followed except that all amounts are scaled for the available amount of Anti5BrdU-EuMac-Peptide-PEGA Conjugate beads. The cleaved EuMac-labeled peptide, with the attached antibody, is removed from the Peptide-PEGA-Beads by washing with 0.267 M HMTA pH 7.5 buffer.

The EuMac-labeled peptide, with the attached antibody, is concentrated by centrifugal filtration with 10,000 mw cut-off filter unit according to the manufacturers literature; it is then passed through a 0.22 micron pore size membrane filter (MILLIPORE Catalog No. GSWP04700, 2000); 20% glycerol is added, and the solution is stored at −20° C. until use.

The combination of Example VIII and Example IX describe the manufacture of a product suitable for commercial use, a tagged-analyte-binding-analyte-binding species, in this case a labeled antibody.

Example X

Luminescence Study of a Eu-Macrocycle-Antibody Conjugate Attached to Apoptotic Cells, Using Gd(III) as Energy Transfer Donor in Cofluorescence Matrix A. Materials
  (a) Phoenix Flow Systems APO-BRDU™ Kit, part number AU 1001.
  (b) The EuMac-labeled peptide, with the attached antibody of Example IX (EuMac-Peptide-Anti5BrdU).
  (c) HMTA 10% aqueous solution adjusted to pH 7.6 with hydrochloric acid (HMTA pH 7.6 buffer).
  (d) DAPI, Molecular Probes, Catalog No. D-1306 (1999).
B. Procedure
1. The first part of this procedure consists of the suspension staining of BrdU-containing cells with EuMac-Antibody and DAPI.
  (a) The positive and negative control cells of the APO-BRDU™ Kit are resuspended by swirling the vials. A one mL aliquot of each control cell suspension (approximately $1 \times 10^6$ cells) is removed and placed in a $12 \times 75$ mm flow cytometry centrifuge tube. The tubes are centrifuged (300×g) for 5 minutes and the 70% (v/v) ethanol supernatant is remove by aspiration, being careful to not disturb the cell pellets.
  (b) The positive and negative control cells are resuspended in 1 mL of HMTA pH 7.6 buffer. The cells are centrifuged as before and the supernatant is removed by aspiration.
  (c) The procedures of step (b) are repeated.
  (d) The antibody labeling solution is prepared by combining 5 uL of EuMac-Peptide-Anti5BrdU with 95 uL of the HMTA pH 7.6 buffer.
  (e) The positive control cell pellets are resuspended in 0.1 mL of the antibody labeling solution, the centrifuge tube is wrapped with aluminum foil, and the cells are incubated in the dark for 30 minutes at room temperature.
  (f) The negative control cell pellets are resuspended in 0.1 mL of the HMTA pH 7.6 buffer, the centrifuge tube is wrapped with aluminum foil, and the cells are incubated in the dark for 30 minutes at room temperature.
  (g) 0.9 mL of a 2 uM DAPI solution (0.9 mL of 2 uM solution) is added to the tubes which contain the positive and negative control cells. The cells are incubated in the dark for a further 30 minutes at room temperature.
2. The second part of this procedure consists of the centrifugal cytology and fluorescence microscopy of the dual stained cells.
  (a) A 1 mL sample of each of the two cell suspensions of step (1.g) is decanted into a Leif Centrifugal Cytology Bucket, R. C. Leif, 2000 (Ref. 40) and is centrifuged at 300×g for ten minutes at room temperature. The cells are sedimental onto and bound to an aminosilane treated slide, Labscientific, Inc. Livingston, N.Y.
  (b) The supernatants are removed by aspiration from the Centrifugal Cytology Bucket sample block; and 0.2 mL of the cofluorescence solution is added to the fixative chambers connecting to the cell containing sample chambers of the Centrifugal Cytology Bucket sample block.
  (c) The Centrifugal Cytology Bucket is centrifuged at 300×g for five minutes at room temperature, the sample block is separated from the slide, and a cover-glass is placed over the dispersions of fixed, stained cells.
  (d) The cells are then viewed with a fluorescence microscope under episcopic illumination with mercury are excitation. The excitation filter passes 365 nm which is reflected by a 400 nm dichroic mirror and excites the europium macrocycle. The emitted red light passes through the dichroic mirror and a 619 nm narrow band-pass filter. The EuMac-Peptide-Anti5BrdU bound to the incorporated 5BrdU is then observed and measured. The DAPI stained DNA in the nucleus is observed or measured through a broad-band emission 450 nm filter. The positive control cells show both a strong red and a blue nuclear emission; the negative control cells show only a blue nuclear emission. Surprisingly, no background binding of the EuMac-Peptide-Anti5BrdU is detected. The $1.20 \times 10^{-4}$ M. Gd(III) cation of the cofluorescence solution blocks the nonspecific binding of the positively charged EuMac.

Example X describes a cytological assay based on a commercially available kit with the use of a tagged-analyte-binding species, in this case a labeled antibody.

Example XI

Simultaneous Use of Two Lanthanide Tags as Secondary Reagents for Comparative Genomic Hybridization Measurements In this Example, methods of this invention to analyze genomes by Comparative Genomic Hybridization (CGH) are exemplified by employing two luminescence species that are each attached to a secondary reagent. This procedure is based on U.S. Pat. No. 5,976,790. Pinkel et al. (Ref. 41) which describes the following steps for CGH:
1. Removal of Repetitive Sequences and/or Disabling the Hybridization Capacity of Repetitive Sequences.
2. Labeling the Nucleic Acid Fragments of the Subject Nucleic Acids.
3. In Situ Hybridization.

Pinkel et al. 1999 (Ref. 41) summarize In Situ Hybridization as: "Generally in situ hybridization comprises the following major steps: (1) fixation of tissue or biological structure to be examined, (2) prehybridization treatment of the biological structure to increase accessibility of target DNA, and to reduce nonspecific binding, (3) hybridization of the mixture of nucleic acids to the nucleic acid in the biological structure or tissue; (4) posthybridization washes to remove nucleic acid fragments not bound in the hybridization and (5) detection of the hybridized nucleic acid fragments."

These authors state that their present technique is limited: "At the current stage of development of CGH, sensitivity is primarily limited by the granularity of the hybridization signals in the metaphase chromosomes. Further improvements in sensitivity will be achieved by optimization of the probe concentration and labeling, and by the averaging of the green-to-red fluorescence ratios from several metaphase spreads."

A. Materials
  (a) SmMac-mono-NCS is synthesized according to the procedures of Examples XI and XXXVI B Step 1 of U.S. Pat. No. 5,696,240, with the substitution of Sm(III) for Eu(III).
  (b) SmMac-labeled peptide with attached avidin is produced by the procedures of Example VIII and Example IX, with the substitution of the SmMac-mono-NCS for the EuMac-mono-NCS and the substitution of Avidin for Anti5BrdU. The SmMac-labeled peptide with attached Avidin will be referred to as SmMac-Peptide-Avidin.

(c) The EuMac-labeled peptide with attached anti-digoxigenin, is produced by the procedures of Example VIII and Example IX with the substitution of anti-digoxigenin for Anti5BrdU. This peptide will be referred to as EuMac-Peptide-anti-digoxigenin.

(d) All other materials are as described in U.S. Pat. No. 5,976,790

B. Procedure (a) The procedure of Kallioniemi et al. 1994 (Ref. 42) is followed. The target metaphase slides are prepared from phytohaemagglutinin-stimulated peripheral blood lymphocytes from a normal male. To assess the hybridization characteristics, each batch of slides is extensively tested with labeled normal genomic DNA and with whole chromosome-painting probes. If evidence of dim or non-uniform hybridization is detected, the entire batch of slides is abandoned, and another batch is prepared.

(b) A DNA sample from abnormal tissue is labeled with biotin-14-dATP (test sample). A second DNA sample from normal tissue is labeled with digoxigenin-11-dUTP (normal reference DNA) using the Bionick labeling system (BRL).

(c) The amounts of DNase and DNA polymerase I are adjusted so that the probe-fragment-size distribution after labeling is 600-2000 base pairs (a smear in a non-denaturing agarose gel). Probe fragments of this size are necessary to obtain uniform, intense hybridization.

(d) Sixty to 100 ng of each of the labeled probes and 5 μg of unlabeled Cot-1 DNA are precipitated with ethanol.

(e) The DNAs are dissolved in 10 uL of hybridization buffer [50% (vol/vol) formamide/10% (wt/vol) dextran sulfate/2× standard saline/citrate, pH 7], denatured at 70° C. for 5 min, and incubated at 37° C. for 30 min.

(f) Metaphase slides are denatured in 70% formamide/2× standard saline/citrate, pH 7 at 70° C. for 3 min, dehydrated sequentially in 70%, 85%, and 100% ethanol, treated with Proteinase K (0.1 μg/mL in 20 mM Tris/2 mM CaCl$_2$, pH 7.5) at 37° C. for 7.5 min, and dehydrated again.

(g) The hybridization mixture is applied on slides and hybridized for 2-3 days at 37° C. in a moist chamber.

(h) After hybridization, the slides are washed and stained by using a single layer of SmMac-Peptide-Avidin (to visualize bound biotinylated probes) at 5 μg/mL and EuMac-Peptide-anti-digoxigenin at 1 μg/mL (to visualize bound digoxigenin-labeled probes).

(i) Samples are counterstained with DAN in an anti-fade solution.)

(j) The slide is dipped in the cofluorescence solution and a coverslip is applied.

(k) The chromosomes are imaged and their emission intensity is measured with a fluorescence microscope with episcopic illumination and equipped with a digitized camera. The 365 nm exciting radiation from a mercury lamp is separated from the luminescence emission of the chromosomes by a dichroic mirror that reflects half the lii ht at 400 nm. The movable emission filter holder has at least 3 filters: a wide band 450 filter for DAPI, a narrow 619 nm filter for the Eu(III) emission, and a 599 and 644 nm filter for the Sm(III) emission. The band widths of the emission filters are 10 nm full-width at half maximum.

(l) The individual chromosomes are identified by the DAPI banding and their size. The signal-to-noise ratio of both the Eu(III) and Sm(III) emission, and the lack of overlap between the two spectra, increases the precision of the measurements permitting probe-fragments smaller than 600 base pairs to be used and eliminating the need for signal averaging from multiple chromosomes of the same type.

Example XII

Synthesis of A Europium Macrocycle Labeled Peptide-Substituted Polynucleotide

A. Materials (a) The Proteinase K cleavable peptide (SEQ ID NO: 1) shown in Formula XIV is synthesized employing an amino-PEGA support similar to that described Example IV, Peptide-PEGA-Beads. A schematic representation of the second lot of the Peptide-PEGA-Beads is shown in Formula XIV:

Formula XIV

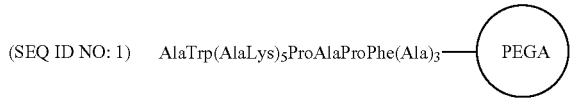

(SEQ ID NO: 1)   AlaTrp(AlaLys)$_5$ProAlaProPhe(Ala)$_3$— PEGA

The peptide (SEQ ID NO: 1) in Formula XIV has the number of lysines increased from the 3 of Example IV to 5 and a spacer amino acid, alanine, interspersed to facilitate both the reaction of the EuMac-mono-NCS with the lysines and the subsequent interaction with the cofluorescence solution.

B. Procedure

An oligonucleotide carrying a EuMac-labeled-polypeptide tail is synthesized by the procedure developed by Haralambidis et al. 1990A (Ref. 4) for the synthesis of carboxyfluorescein conjugates of both peptide-oligodeoxyribo-nucleotides and polyamide-oligonucleotides. According to this procedure, which employs a commercially available automated DNA synthesizer (Applied Biosystems Inc.), the following steps are performed:

(a) The terminal amino group of the Peptide-PEGA-Beads is converted to an amide by reaction with an α,ω-hydroxycarboxylic acid derivative, the structure 2 of Haralambidis et al. 1990A. The hydroxyl group of the acid is previously protected by conversion to a 9-phenylxanthene-9-yl(pixyl) ether and the carboxyl terminus is activated as the p-nitrophenyl ester.

(b) The hydroxyl group which now terminates the peptide is deprotected; it is then esterified with a phosphoramidate, and the bead-linked-peptide-conjugated polynucleotide is subsequently assembled by sequential reaction with methyl N,N-diisopropyl nucleoside phosphoramidates to a 30 mer. This 30 mer oligonucleotide (SEQ ID NO: 2) is described by Haralambidis et al. 1990A as being d(GGGCTTCACAACATCTGTGAT-GTCAGCAGG). Protected lysine residues are included in both the peptide and the polyamide to provide primary amino functionalities suitable for conjugation with an isothiocyanate.

(c) The primary amino groups of the lysine residues of the bead-linked-peptide-conjugated polynucleotide are deprotected and the lysines are coupled to multiple EuMac-mono-NCS according to the procedures of Example VII.

(d) The EuMac-labeled-bead-linked-peptide-conjugated polynucleotide is released from the PEGA beads by enzymatic hydrolysis with Proteinase K by the procedures of Example VII

Example XIII

Hybridization and Detection of a Europium Macrocycle Labeled Peptide-Substituted Polynucleotide A. Materials
  (a) The EuMac-labeled-bead-linked-peptide-conjugated polynucleotide of Example XII (EuMac-Peptide-Polynucleotide).
  (b) An aqueous solution containing NaCl (0.75 M), sodium citrate (0.075M), $NaH_2PO_4$ (25 mM), $Na_2HPO_4$ (25 mM), tetrasodium pyrophosphate (10 mM), disodium adenosine triphosphate (0.1 mM) SIGMA®, Catalog No. A 7699 (1998), salmon testes DNA (25 mg/L, SIGMA®, Catalog No. D 1626 (1998), FICOLL® (0.01% w/v), SIGMA®, Catalog No. F 2637 (1998), polyvinylpyrrolidone (0.01%), SIGMA®, Catalog No. PD 5288 (1998), bovine serum albumin (0.01%), SIGMA®, Catalog No. B 4287 (1998), and 20% N,N-dimethylformamide, SIGMA®, Catalog No. D 7656 (1998), (hybridization buffer).
  (c) The 3.7 Kb plasmid derived from pUC and containing a 1 kb mouse renal kallikrein cDNA insert of Haralambidis et al. 1990B (Ref. 5) (Plasmid Positive Control).
  (d) The similar pUC plasmid containing the metallothionein IIA gene promoter spliced with the chloramphenicol acetyl transferase (CAT) structural gene of Haralambidis et al. 1990B (Ref 5) (Plasmid Negative Control).
  (e) Herring sperm DNA, SIGMA®, Catalog No. D 7290 (1998).
  (f) Nitrocellulose membranes (SIGMA®, Catalog No. Z36,022-8 (1998).

B. Procedure

The procedures of Haralambidis et al. 1990B (Ref. 5) are followed with the exception of the substitution of the EuMac-Peptide-Polynucleotide for the fluorescein-labeled peptide-substituted poly-nucleotide of Haralambidis et al. 1990B (Ref. 5). Hybridization experiments with the EuMac-Peptide-Polynucleotide conjugate probes are carried out onto clot blots containing 3.7 kb plasmid positive and negative controls. Each clot contains also 1 μg of herring sperm DNA.

(a) The nitrocellulose membranes are prehybridized at 42° C. for 6.5 h in 10 mL of hybridization buffer.
  (b) 100 ng of the EuMac-Peptide-Polynucleotide is then added and it is allowed to hybridize at 42° C. overnight.
  (c) The filters are washed four times, for ten minutes each, at 42° C. in 0.2×SSC (0.03 M NaCl, 0.003 M sodium citrate).
  (d) The filters are gently wetted with the cofluorescence solution and allowed to air-dry.
  (e) The filters are examined under ultraviolet light (365 nm band). The Plasmid Positive Control emits a red glow. The emission of the Plasmid Negative Control is much weaker.

These results with the lanthanide(III) complexes show an additive effect; the luminescence is proportional to the total number of lanthanide(III) macrocycles bound to the peptide. This is totally different from the extremely low (0.05 to 0.002) ratio between the fluorescence of fluorescein tags on a polymer and the fluorescence of the fluorescein monomer observed by Haralambidis et al. 1990B (Ref. 5). Thus, where a conventional organic fluorophore did not work, an example of the new tagged-analyte-binding species will work; specifically with multiple lanthanide(III) macrocycles (EuMac) bound to a peptide.

The Peptide-PEGA-Beads with free hydroxyl groups which are formed by converting the alpha amino groups into an amide by reaction with an α,ω-hydroxycarboxylic acid derivative can be stored. If tags that are stable to the nucleic acid synthesis and deprotection reactions are used, tagged Peptide-PEGA-Beads with free hydroxyl groups can be stored and subsequently extended. The use of an enzymatic cleavage minimizes the degradation of tags that can not withstand harsh treatments. The free hydroxyl groups can be extended with short nucleotide sequences, which after binding to a complementary region of a large template can be enzymatically extended (Strachan and A. P. Read, 1999 (Ref. 29)).

---

The invention claimed is:

1. A water-soluble polymer linked to a solid support, comprising:
- a solid support optionally comprising a spacer sequence comprising one or more spacer monomer units attached to the solid support; and
- a water-soluble polymer covalently linked to the solid support or to the spacer sequence, the water-soluble polymer comprising
  - a first cleavage segment of known composition and/or sequence comprising at least one monomer unit comprising a selectively cleavable link to the solid support or to the spacer sequence, wherein cleavage of the selectively cleavable link separates the water-soluble polymer from the solid support,
  - a second segment of known composition and/or sequence comprising at least one monomer unit selected from the group consisting of a monomer unit linked to a reactive functionality able to be covalently coupled to a tag and a monomer unit linked to a tag,
  - a third segment of known composition and/or sequence comprising one or more monomer units linked to a reactive functionality that can form a covalent bond with a member of a specific combining pair, and
  - optionally one or more spacer monomer units provided adjacent to any segment and/or between any two segments and/or within any one or more of the second segment and the third segment.

2. The water-soluble polymer linked to a solid support of claim 1, wherein the second segment of known composition and/or sequence comprises at least one monomer unit selected from the group consisting of a monomer unit linked to a reactive functionality and a monomer unit linked to a tag.

3. The water-soluble polymer linked to a solid support of claim 2, wherein the cleavage of the selectively cleavable link does not decompose the tag.

4. The water-soluble polymer linked to a solid support of claim 1, wherein the third segment of known composition and/or sequence comprises one or more monomer units linked to a reactive functionality covalently bound to a member of a specific combining pair.

5. The water-soluble polymer linked to a solid support of claim 4, wherein the cleavage of the selectively cleavable link does not sever the linkage of the covalently bound member of a specific combining pair from the polymer or interfere with the formation of the combining pair.

6. The water-soluble polymer linked to a solid support of claim 1, wherein the solid support is a water-insoluble, swellable functionalized bead having a dry particle size in the range from 10 to 500 microns and at least one of the monomers of the polymer includes a functionalized hydrophobic side chain.

7. The water-soluble polymer linked to a solid support of claim 6, wherein the solid support comprises a spacer sequence comprising one or more spacer monomer units attached to the solid support.

8. The water-soluble polymer linked to a solid support of claim 2, wherein the reactive functionalities of the water-soluble polymer are independently selected from the group consisting of amino, azide, alcoholic hydroxyl, phenolic hydroxyl, aldehyde, carboxylic acid, carboxamide, halogen, isocyanate, isothiocyanate, mercapto, activated disulfide, nitrile, functionalized alkyl, functionalized aryl, and functionalized alkyl-substituted aryl substituents.

9. The water-soluble polymer linked to a solid support of claim 1, wherein the third segment comprises at least one monomer unit having a reactive functionality linked to an analyte-binding species or an analyte.

10. The water-soluble polymer linked to a solid support of claim 4, wherein the member of a specific combining pair able to form a covalent bond with the reactive functionality of the third segment is selected from the group consisting of an analyte-binding species or an analyte.

11. The water-soluble polymer linked to a solid support of claim 1, wherein the water-soluble polymer consists essentially of monomer units able to undergo synthesis on a solid support, the monomer units being selected from the group consisting of amino acids, peptide nucleic acids, nucleotide monophosphate monomer units, and sugar monomer units.

12. The water-soluble polymer linked to a solid support of claim 1, wherein the first cleavage segment comprises a sequence of at least two linked monomer units, each monomer unit selected from the group consisting of an amino acid monomer, a sugar monomer and a nucleotide, and wherein the water-soluble polymer is selectively cleavable from said support in the presence of an enzyme.

13. The water-soluble polymer linked to a solid support of claim 12, wherein the first cleavage segment comprises at least one disulfide linked monomer units that is selectively cleavable from said support in the presence of a reducing agent.

14. The water-soluble polymer linked to a solid support of claim 12, wherein the cleavage segment is a substrate for the enzyme and the enzyme is selected from the group consisting of a proteinase, an endonuclease and a glycosidase.

15. The water-soluble polymer linked to a solid support of claim 2, wherein at least one tag is selected from the group consisting of an optical-label, an other-label, or a separation-tag.

16. The water-soluble polymer linked to a solid support of claim 15, wherein at least one tag is an optical-label.

17. The water-soluble polymer linked to a solid support of claim 16, wherein the second segment comprises at least a first monomer unit having a first optical-label and a second monomer unit having a second optical-label, wherein the first optical-label is different from the second optical-label.

18. The water-soluble polymer linked to a solid support of claim 17, wherein the first optical-label is a luminescence enhancer and the second optical-label is a lanthanide complex.

19. The water-soluble polymer linked to a solid support of claim 17, wherein the first optical-label is capable of transferring energy to the second optical-label.

20. The water-soluble polymer linked to a solid support of claim 19, wherein the second segment further comprises at least a third monomer having a third optical-label different from the first and the second optical-labels, the optical-labels being ordered into pairs with the emission of a first optical-label overlapping the excitation of the second optical-label, the emission of the second optical-label overlapping the excitation of the third optical-label; and wherein the ordering of monomer units produces a relative orientation and spacing of the optical-labels to maximize energy transfer between the optical-label with the shortest excitation wavelength and the optical-label with the longest emission wavelength.

21. The water-soluble polymer linked to a solid support of claim 20, wherein each of the first, second, and third optical-labels is an independent species that emits light in a range of from 300 to 1,400 nanometers after receiving energy in a range of from 200 to 1,000 nanometers.

22. The water-soluble polymer linked to a solid support of claim 17, wherein the first optical-label and second optical-label are sequentially ordered to control their interactions.

23. The water-soluble polymer linked to a solid support of claim 11, wherein the monomer units comprise amino acid monomer units linked by amide linkages.

24. The water-soluble polymer linked to a solid support of claim 23, wherein each reactive functionality is independently selected from the group consisting of amino, azide, alcoholic hydroxyl, phenolic hydroxyl, aldehyde, carboxylic acid, carboxamide, halogen, isocyanate, isothiocyanate, mercapto, activated disulfide, nitrile, functionalized alkyl, functionalized aryl, and functionalized alkyl-substituted aryl substituents.

25. The water-soluble polymer linked to a solid support of claim 23, wherein at least one tag is an optical-label.

26. The water-soluble polymer linked to a solid support of claim 25, wherein at least one tag is an optical-label that is capable of absorbing light in a certain wavelength range and emitting light in a higher wavelength range.

27. The water-soluble polymer linked to a solid support of claim 25, wherein at least one amino acid monomer unit absorbs light in a range different from that of the optical-label.

28. The water-soluble polymer linked to a solid support of claim 25, wherein the optical-label is a lanthanide compound.

29. The water-soluble polymer linked to a solid support of claim 17, further comprising at least one spacer monomer unit disposed such that the first optical-label has an orientation and spacing relative to the second optical-label to maximize energy transfer between the first and second optical-labels.

30. The water-soluble polymer linked to a solid support of claim 25, wherein the optical-label is capable of absorbing and/or emitting light in a wavelength range of from 200 to 1,400 nanometer.

31. The water-soluble polymer linked to a solid support of claim 30, wherein the optical-label is capable of emitting light in a range of from 300 to 1,400 nanometers.

32. The water-soluble polymer linked to a solid support of claim 30, wherein the optical-label is capable of absorbing light in a range of from 200 to 1,000 nanometers.

33. The water-soluble polymer linked to a solid support of claim 17, wherein the first optical-label is capable of transferring energy to the second optical-label.

34. The water-soluble polymer linked to a solid support of claim 28, wherein the lanthanide compound is a lanthanide complex.

35. The water-soluble polymer linked to a solid support of claim 34, wherein the lanthanide complex is a lanthanide macrocycle.

36. The water-soluble polymer linked to a solid support of claim 34, wherein the lanthanide complex includes at least one enhancer.

37. The water-soluble polymer linked to a solid support of claim 28, wherein the lanthanide compound is selected from the group consisting of a compound of europium, a compound of samarium, a compound of terbium, and a compound of dysprosium.

38. The water-soluble polymer linked to a solid support of claim 28, wherein the lanthanide compound is an energy transfer acceptor lanthanide macrocycle compound having an excitation spectrum maximum in a range of from 200 to 700 nanometers.

39. The water-soluble polymer linked to a solid support of claim 36, wherein the enhancer of an energy transfer acceptor lanthanide macrocycle complex having an excitation spectrum maximum in a range of from 200 to 700 nanometers.

40. The water-soluble polymer linked to a solid support of claim 28, wherein the lanthanide compound is an energy transfer acceptor lanthanide macrocycle complex having an emission spectrum maximum in a range of from 500 to 1400 nanometers.

41. The water-soluble polymer linked to a solid support of claim 36, wherein the lanthanide compound accepts energy from a luminescence enhancer.

42. The water-soluble polymer linked to a solid support of claim 36, wherein the lanthanide complex accepts energy from a luminescence enhancer.

43. The water-soluble polymer linked to a solid support of claim 41, wherein a second lanthanide ion is involved with the transfer of energy to the lanthanide complex.

44. The water-soluble polymer linked to a solid support of claim 18, wherein the lanthanide complex has an orientation and spacing relative to the luminescence enhancer so as to maximize the emission of light.

45. The water-soluble polymer linked to a solid support of claim 18, wherein the luminescence enhancer is selected from the group consisting of a beta-diketone, a beta-diketonate, and a mixture thereof.

46. The water-soluble polymer linked to a solid support of claim 33, wherein the first optical-label and the second optical-label are an organic optical-label pair.

47. The water-soluble polymer linked to a solid support of claim 46, wherein the second optical-label after receiving energy from the first optical-label, emits light in a range of from 300 to 1,400 nanometers.

48. The water-soluble polymer linked to a solid support of claim 15, wherein the at least one tag is an other-label.

49. The water-soluble polymer linked to a solid support of claim 48, wherein the other-label is radioactive.

50. The water-soluble polymer linked to a solid support of claim 48, wherein the other-label is paramagnetic.

51. The water-soluble polymer linked to a solid support of claim 15, wherein the at least one tag is a separation-tag.

52. The water-soluble polymer linked to a solid support of claim 51, wherein the separation-tag is a moiety that increases magnetic susceptibility, ionic charge, mass, or density.

53. The water-soluble polymer linked to a solid support of claim 15, wherein the second segment comprises at least one tag that is an optical-label and one or more tags independently selected from the group consisting of an other-label and a separation-tag.

54. The water-soluble polymer linked to a solid support of claim 10, wherein the third segment further comprises an analyte-binding species covalently bound to the reactive functionality, and wherein the analyte-binding species is selected from the group consisting of
- an antibody,
- a protein,
- a nucleic acid,
- a peptide nucleic acid,
- a polysaccharide, and
- a haptene having a molecular weight in the range of from 125 to 2,000 daltons.

55. The water-soluble polymer linked to a solid support of claim 54, wherein the antibody is a polyclonal antibody or a monoclonal antibody.

56. The water-soluble polymer linked to a solid support of claim 54, wherein the nucleic acid is DNA or RNA.

57. The water-soluble polymer linked to a solid support of claim 11, wherein the polymer is a dendrimer.

58. The water-soluble polymer linked to a solid support of claim 6, wherein the polymer is a dendrimer.

* * * * *